United States Patent
Johnson

(10) Patent No.: US 11,037,260 B2
(45) Date of Patent: Jun. 15, 2021

(54) EMERGENCY RESPONSE SYSTEM

(71) Applicant: ZOLL Medical Corporation, Chelmsford, MA (US)

(72) Inventor: Guy R. Johnson, Gloucester, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 419 days.

(21) Appl. No.: 15/079,371

(22) Filed: Mar. 24, 2016

(65) Prior Publication Data
US 2016/0284038 A1    Sep. 29, 2016

Related U.S. Application Data

(60) Provisional application No. 62/138,538, filed on Mar. 26, 2015.

(51) Int. Cl.
| | |
|---|---|
| *G06Q 50/26* | (2012.01) |
| *G16H 15/00* | (2018.01) |
| *G16H 50/00* | (2018.01) |
| *G06Q 10/06* | (2012.01) |
| *G01C 21/00* | (2006.01) |

(52) U.S. Cl.
CPC ....... *G06Q 50/265* (2013.01); *G01C 21/3804* (2020.08); *G01C 21/3896* (2020.08); *G06Q 10/06* (2013.01); *G16H 15/00* (2018.01); *G16H 50/00* (2018.01)

(58) Field of Classification Search
CPC ...... G06Q 50/265; G06Q 10/06; G16H 15/00; G16H 50/00; G01C 21/3804
See application file for complete search history.

(56) References Cited

U.S. PATENT DOCUMENTS

| | | | |
|---|---|---|---|
| 5,166,972 A | 11/1992 | Smith | |
| 5,960,337 A | 9/1999 | Brewster et al. | |
| 6,985,771 B2* | 1/2006 | Fischell | A61B 5/4839 |
| | | | 607/3 |

(Continued)

FOREIGN PATENT DOCUMENTS

| | | |
|---|---|---|
| JP | 08-005394 | 1/1996 |
| JP | 2002-230672 | 8/2002 |

OTHER PUBLICATIONS

Vlad Savov, "Samsung navigates away from Google with Here maps for Galaxy phones", The Verge, Aug. 29, 2014, https://www.theverge.com/2014/8/29/6082067/samsung-navigates-away-from-google-with-here-maps-for-galaxy-phones (Year: 2014).*

(Continued)

*Primary Examiner* — Gerardo Araque, Jr.
(74) *Attorney, Agent, or Firm* — Fish & Richardson P.C.

(57) ABSTRACT

A system includes a processor coupled to a memory. The processor and memory are configured to, during an emergency situation, initiate presentation, on a user interface, of information indicative of a location of one or more shelters. The processor and memory are configured to, during the emergency situation, receive, from a server, data indicative of actual occupancy of at least one of the one or more shelters. The processor and memory are configured to enable a rescuer to access information, through the user interface, about one or more of a potential occupancy and the actual occupancy of the at least one of the one or more shelters.

62 Claims, 7 Drawing Sheets

(56) References Cited

U.S. PATENT DOCUMENTS

| | | | | |
|---|---|---|---|---|
| 8,587,476 B2* | 11/2013 | Hung | | G01S 19/14 342/357.74 |
| 8,671,106 B1* | 3/2014 | Lee | | G06F 16/90324 707/767 |
| 9,232,040 B2 | 1/2016 | Barash et al. | | |
| 2002/0143469 A1* | 10/2002 | Alexander | | A62B 99/00 702/2 |
| 2003/0125998 A1* | 7/2003 | McKenney | | G06Q 10/06 705/324 |
| 2004/0153222 A1* | 8/2004 | Puchkoff | | B63B 49/00 701/21 |
| 2005/0070247 A1* | 3/2005 | Larson | | H04M 11/04 455/404.1 |
| 2005/0190053 A1* | 9/2005 | Dione | | G08B 21/22 340/500 |
| 2005/0245232 A1* | 11/2005 | Jakober | | G08B 27/005 455/410 |
| 2006/0227047 A1* | 10/2006 | Rosenberg | | G01S 5/0072 342/357.55 |
| 2007/0055559 A1* | 3/2007 | Clawson | | G06Q 10/08 705/325 |
| 2007/0219420 A1* | 9/2007 | Moore | | G06Q 10/00 600/300 |
| 2007/0288208 A1* | 12/2007 | Grigsby | | G06Q 10/06 703/2 |
| 2008/0319805 A1* | 12/2008 | Burke, Jr. | | G06Q 10/02 705/5 |
| 2010/0241349 A1* | 9/2010 | Wu | | G06Q 10/06 701/533 |
| 2010/0295656 A1* | 11/2010 | Herickhoff | | G06Q 50/265 340/3.1 |
| 2010/0324616 A1* | 12/2010 | Livnat | | A61M 5/14276 607/6 |
| 2011/0181443 A1* | 7/2011 | Gutierrez | | G01C 21/3691 340/990 |
| 2011/0307264 A1* | 12/2011 | Hitney | | G06Q 10/06 705/2 |
| 2012/0190295 A1* | 7/2012 | Kim | | G08B 21/10 455/3.01 |
| 2013/0103313 A1* | 4/2013 | Moore | | G01C 21/3673 701/533 |
| 2013/0257613 A1* | 10/2013 | Jarman | | G08B 25/016 340/539.11 |
| 2013/0278420 A1* | 10/2013 | Araiz-Boys | | G08B 25/12 340/539.18 |
| 2014/0002241 A1* | 1/2014 | Elghazzawi | | H04W 4/023 340/8.1 |
| 2014/0038544 A1* | 2/2014 | Jones | | G08B 13/196 455/404.2 |
| 2014/0203909 A1* | 7/2014 | Elgebaly | | H04W 4/21 340/8.1 |
| 2014/0249850 A1* | 9/2014 | Woodson | | G16H 20/00 705/3 |
| 2014/0314212 A1* | 10/2014 | Bentley | | H04M 3/5116 379/38 |
| 2014/0320282 A1* | 10/2014 | Zhang | | G08B 7/066 340/502 |
| 2014/0365390 A1* | 12/2014 | Braun | | H04W 4/023 705/325 |
| 2015/0213225 A1* | 7/2015 | Amarasingham | | G06F 19/00 705/2 |
| 2015/0382151 A1* | 12/2015 | Pariani | | H04W 4/04 455/456.3 |
| 2016/0051850 A1* | 2/2016 | Menard | | A62C 35/58 169/16 |
| 2016/0110833 A1* | 4/2016 | Fix | | G06Q 50/265 705/324 |
| 2017/0273116 A1 | 9/2017 | Elghazzawi | | |

OTHER PUBLICATIONS

FEMA, "Risk Management Series Design Guidance for Shelters and Safe Rooms Providing Protection to People and Buildings Against Terrorist Attacks", FEMA 453, May 2006 (Year: 2006).*

J. Smalls, Yue Wang, Xi Li, Zehuang Chen and K. W. Tang, "Health monitoring systems for massive emergency situations," 2009 IEEE Long Island Systems, Applications and Technology Conference, Farmingdale, NY, USA, 2009, pp. 1-11 (Year: 2009).*

R. Shad, K. Ur, R. Shad and K. Ur, "Disaster Management and GIS," 2006 International Conference on Advances in Space Technologies, Islamabad, Pakistan, 2006, pp. 6-10 (Year: 2006).*

D. A. Goughnour and R. T. Durbin, "Device Independent Information Sharing During Incident Response," 2008 IEEE Conference on Technologies for Homeland Security, Waltham, MA, USA, 2008, pp. 486-491 (Year: 2008).*

R. Kilgore et al, "A Precision Information Environment (PIE) for emergency responders: Providing collaborative manipulation, role-tailored visualization, and integrated access to heterogeneous data," 2013 IEEE International Conference on Technologies for Homeland Security 2013, pp. 766-771 (Year: 2013).*

* cited by examiner

US 11,037,260 B2

EMERGENCY RESPONSE SYSTEM

CLAIM OF PRIORITY

This application claims priority under 35 USC § 119(e) to U.S. Patent Application Ser. No. 62/138,538, filed Mar. 26, 2015, the entire contents of which are hereby incorporation by reference.

TECHNICAL FIELD

This disclosure relates to an emergency response system, e.g., to assist emergency responders in responding to an emergency situation.

BACKGROUND

An emergency situation, which can be a natural disaster such as a hurricane and earthquake can cause widespread damage, destruction, and injury. Emergency responders, such as ambulance, police, and fire crew, provide emergency response services, such as medical care or rescue operations, during and following the emergency situation.

SUMMARY

In a general aspect, a system includes a processor coupled to a memory. The processor and memory are configured to, during an emergency situation, initiate presentation, on a user interface, of information indicative of a location of one or more shelters. The processor and memory are configured to, during the emergency situation, receive, from a server, data indicative of actual occupancy of at least one of the one or more shelters. The processor and memory are configured to enable a rescuer to access information, through the user interface, about one or more of a potential occupancy and the actual occupancy of the at least one of the one or more shelters.

Embodiments can include one or more of the following features.

The processor and memory are configured to receive, from a server, the information indicative of the location of the one or more shelters and the information indicative of the potential occupancy of the at least one of the one or more shelters. The processor and memory are configured to receive and store the information indicative of the location of the one or more shelters and the information indicative of the potential occupancy of the at least one of the one or more shelters prior to the emergency situation.

The user interface includes a user interface of a mobile computing device, such as a wearable computing device.

The user interface includes a user interface of a medical device, such as a defibrillator.

The information indicative of the potential occupancy of the at least one of the one or more shelters includes one or more of a number of potential occupants of the shelter, an identity of at least one of the potential occupants of the shelter, demographic information about the potential occupants of the shelter, and a medical condition of at least one of the potential occupants of the shelter The data indicative of the actual occupancy of the at least one of the one or more shelters includes one or more of a number of actual occupants of the shelter, an identity of at least one of the actual occupants of the shelter, demographic information about the potential occupants of the shelter, a medical condition of at least one of the actual occupants of the shelter, and a health status of at least one of the actual occupants of the shelter.

The information indicative of the location of the one or more shelters includes one or more of GPS coordinates, an address, a landmark, and a property description.

The processor and memory are configured to: receive an input identifying a particular shelter; and cause display of information indicative of the location of the particular shelter.

The processor and memory are configured to receive the input from the rescuer through the user interface.

The processor and memory are configured to receive the input from a remote computing device.

The processor and memory are configured to identify a particular shelter to which the rescuer can provide rescue services. The processor and memory are configured to identify the particular shelter based on a location of the rescuer and the location of the particular shelter. The processor and memory are configured to identify the particular shelter based on the data indicative of the actual occupancy of the particular shelter. The processor and memory are configured to identify the particular shelter based on one or more of an expertise of the rescuer or a piece of medical equipment available to the rescuer.

The processor and memory are configured to display, on the user interface, directions to a particular shelter based on a location of the rescuer and the location of the particular shelter. The processor and memory are configured to determine the directions based on information indicative of road status. The processor and memory are configured to receive the information indicative of road status during the emergency situation.

The processor and memory are configured to receive, through the user interface, one or more of (i) updated information indicative of the location of a particular shelter and (ii) updated information indicative of the actual occupancy of the particular shelter. The processor and memory are configured to transmit the updated information to a remote computing device.

In a general aspect, a non-transitory computer readable storage medium stores instructions for causing a computing system to, during an emergency situation, initiate presentation, on a user interface, of information indicative of a location of one or more shelters. The instructions cause the computing system to, during the emergency situation, receive, from a server, data indicative of actual occupancy of at least one of the one or more shelters. The instructions cause the computing system to enable a rescuer to access information, through the user interface, about one or more of a potential occupancy and the actual occupancy of the at least one of the one or more shelters.

Embodiments can include one or more of the following features.

The instructions cause the computing system to receive, from the server, the information indicative of the location of the one or more shelters and the information indicative of the potential occupancy of the at least one of the one or more shelters. The instructions cause the computing system to receive and store the information indicative of the location of the one or more shelters and the information indicative of the potential occupancy of the at least one of the one or more shelters prior to the emergency situation.

The user interface includes a user interface of a mobile computing device, such as a wearable computing device.

The user interface includes a user interface of a medical device, such as a defibrillator.

The information indicative of the potential occupancy of the at least one of the one or more shelters includes one or more of a number of potential occupants of the shelter, an identity of at least one of the potential occupants of the shelter, demographic information about the potential occupants of the shelter, and a medical condition of at least one of the potential occupants of the shelter The data indicative of the actual occupancy of the at least one of the one or more shelters includes one or more of a number of actual occupants of the shelter, an identity of at least one of the actual occupants of the shelter, demographic information about the potential occupants of the shelter, a medical condition of at least one of the actual occupants of the shelter, and a health status of at least one of the actual occupants of the shelter.

The information indicative of the location of the one or more shelters includes one or more of GPS coordinates, an address, a landmark, and a property description.

The instructions cause the computing system to receive an input identifying a particular shelter; and cause display of information indicative of the location of the particular shelter.

The instructions cause the computing system to receive the input from the rescuer through the user interface.

The instructions cause the computing system to receive the input from a remote computing device.

The instructions cause the computing system to identify a particular shelter to which the rescuer can provide rescue services. The instructions cause the computing system to identify the particular shelter based on a location of the rescuer and the location of the particular shelter. The instructions cause the computing system to identify the particular shelter based on the data indicative of the actual occupancy of the particular shelter. The instructions cause the computing system to identify the particular shelter based on one or more of an expertise of the rescuer and a piece of medical equipment available to the rescuer.

The instructions cause the computing system to display, on the user interface, directions to a particular shelter based on a location of the rescuer and the location of the particular shelter. The instructions cause the computing system to determine the directions based on information indicative of road status. The instructions cause the computing system to receive the information indicative of road status during the emergency situation.

The instructions cause the computing system to receive, through the user interface, one or more of (i) updated information indicative of the location of a particular shelter and (ii) updated information indicative of the actual occupancy of the particular shelter. The instructions cause the computing system to transmit the updated information to a remote computing device.

In a general aspect, a method includes, during an emergency situation, initiating presentation, on a user interface, of information indicative of the location of one or more shelters. The method includes, during the emergency situation, receiving, from a server, data indicative of actual occupancy of at least one of the one or more shelters. The method includes enabling a rescuer to access information, through the user interface, about one or more of a potential occupancy and the actual occupancy of the at least one of the one or more shelters.

In a general aspect, a system includes a processor coupled to a memory. The processor and memory are configured to provide, to one or more computing devices each associated with a rescuer, data indicative of (i) a location of one or more shelters and (ii) potential occupancy of the one or more shelters. The processor and memory are configured to, during an emergency situation, receive data indicative of actual occupancy of at least one of the one or more shelters. The processor and memory are configured to provide, to the one or more computing devices, the data indicative of the actual occupancy of at least one of the one or more shelters.

Embodiments can include one or more of the following features.

The processor and memory are configured to obtain the data indicative of (i) the location of the one or more shelters and (ii) the potential occupancy of the one or more shelters from a publicly available database.

The processor and memory are configured to provide, to one of the computing devices, data indicative of (i) a location of a particular shelter and (ii) potential occupancy of the particular shelter responsive to a request received from the computing device.

The processor and memory are configured to identify a particular shelter to which a particular rescuer can provide rescue services. The processor and memory are configured to identify the particular shelter based on a location of the computing device associated with the rescuer and the data indicative of the location of the particular shelter. The processor and memory are configured to identify the particular shelter based on one or more of an expertise of the rescuer and a piece of medical equipment available to the rescuer.

In a general aspect, a non-transitory computer readable storage medium storing instructions for causing a computing system to provide, to one or more computing devices each associated with a rescuer, data indicative of (i) a location of one or more shelters and (ii) potential occupancy of the one or more shelters. The instructions cause the computing system to, during an emergency situation, receive data indicative of actual occupancy of at least one of the one or more shelters. The instructions cause the computing system to provide, to the one or more computing devices, the data indicative of the actual occupancy of at least one of the one or more shelters.

Embodiments can include one or more of the following features.

The instructions cause the computing system to obtain the data indicative of (i) the location of the one or more shelters and (ii) the potential occupancy of the one or more shelters from a publicly available database.

The instructions cause the computing system to provide, to one of the computing devices, data indicative of (i) a location of a particular shelter and (ii) potential occupancy of the particular shelter responsive to a request received from the computing device.

The instructions cause the computing system to identify a particular shelter to which a particular rescuer can provide rescue services. The instructions cause the computing system to identify the particular shelter based on a location of the computing device associated with the rescuer and the data indicative of the location of the particular shelter. The instructions cause the computing system to identify the particular shelter based on one or more of an expertise of the rescuer or a piece of medical equipment available to the rescuer.

In a general aspect, a method includes providing, to one or more computing devices each associated with a rescuer, data indicative of (i) a location of one or more shelters and (ii) potential occupancy of the one or more shelters. The method includes, during an emergency situation, receiving data indicative of actual occupancy of at least one of the one or more shelters. The method includes providing, to the one or more computing devices, the data indicative of the actual occupancy of at least one of the one or more shelters.

In a general aspect, a defibrillating system includes a processor coupled to a memory. The processor and memory are configured to receive identifiers of one or more shelters. The processor and memory are configured to, during an emergency situation, display, on a user interface of the defibrillating system, information indicative of (i) the location of the shelters and (ii) one or more of potential occupancy and actual occupancy of the one or more shelters. The processor and memory are configured to, based on a location of the defibrillating system and the information indicative of the location of a particular shelter, provide directions to the particular shelter. The processor and memory are configured to receive, through the user interface of the defibrillating system, updated information indicative of the actual occupancy of the particular shelter; and transmit the updated information indicative of the actual occupancy of the particular shelter to a remote computing device.

Embodiments can include one or more of the following features.

The processor and memory are configured to receive the information indicative of (i) the location of the one or more shelters and (ii) the potential occupancy of the one or more shelters prior to the emergency situation.

The processor and memory are configured to request the information responsive to receiving the identifiers of the one or more shelters.

The directions include one or more of driving directions to the particular shelter and a description of the location of the particular shelter.

The defibrillating system includes a defibrillation device.

Other aspects, features, and advantages will be apparent from the description and drawings, and from the claims.

DETAILED DESCRIPTION

Emergency responders, such as emergency medical technicians (EMTs), firefighters, ambulance, or volunteer responders, are organized responders who provide rescue and emergency response services, e.g., to a particular geographic area. In the system described here, a central server can provide information to emergency responders that can help the responders in responding efficiently to a disaster, such as a hurricane, a tornado, an earthquake, or another type of disaster. For instance, the central server can provide responders with information about the location of shelters where people may have taken refuge from the disaster. The central server can provide responders with information about potential or actual occupants of a shelter, such as information about a number of occupants, a medical condition of the occupants, or other information. Based on the information provided by the central server, an emergency responder can efficiently locate a shelter and gain an understanding of the situation he may encounter at the shelter.

Occupants of a shelter can provide status updates to the central server, e.g., to indicate who is present in the shelter and what is their condition (e.g., healthy, injured). Emergency responders can also provide status updates following their visit to a shelter. The information from the status updates can be used, e.g., in coordinating the activities of other emergency responders. In some examples, the status of shelter occupants can be made available, e.g., to relatives curious to know whether a loved one has been hurt in a disaster.

In some examples, the central server can provide guidance to the emergency responders in responding to the disaster. For instance, the central server can provide directions to a shelter, e.g., based on real time information about road closures. The central server can plot an itinerary that enables an emergency responder to efficiently visit multiple shelters. The central server can assign a responder to visit a particular shelter, e.g., based on the responder's location relative to the shelter, the responder's expertise, or medical equipment available to the shelter.

Figure 1A:
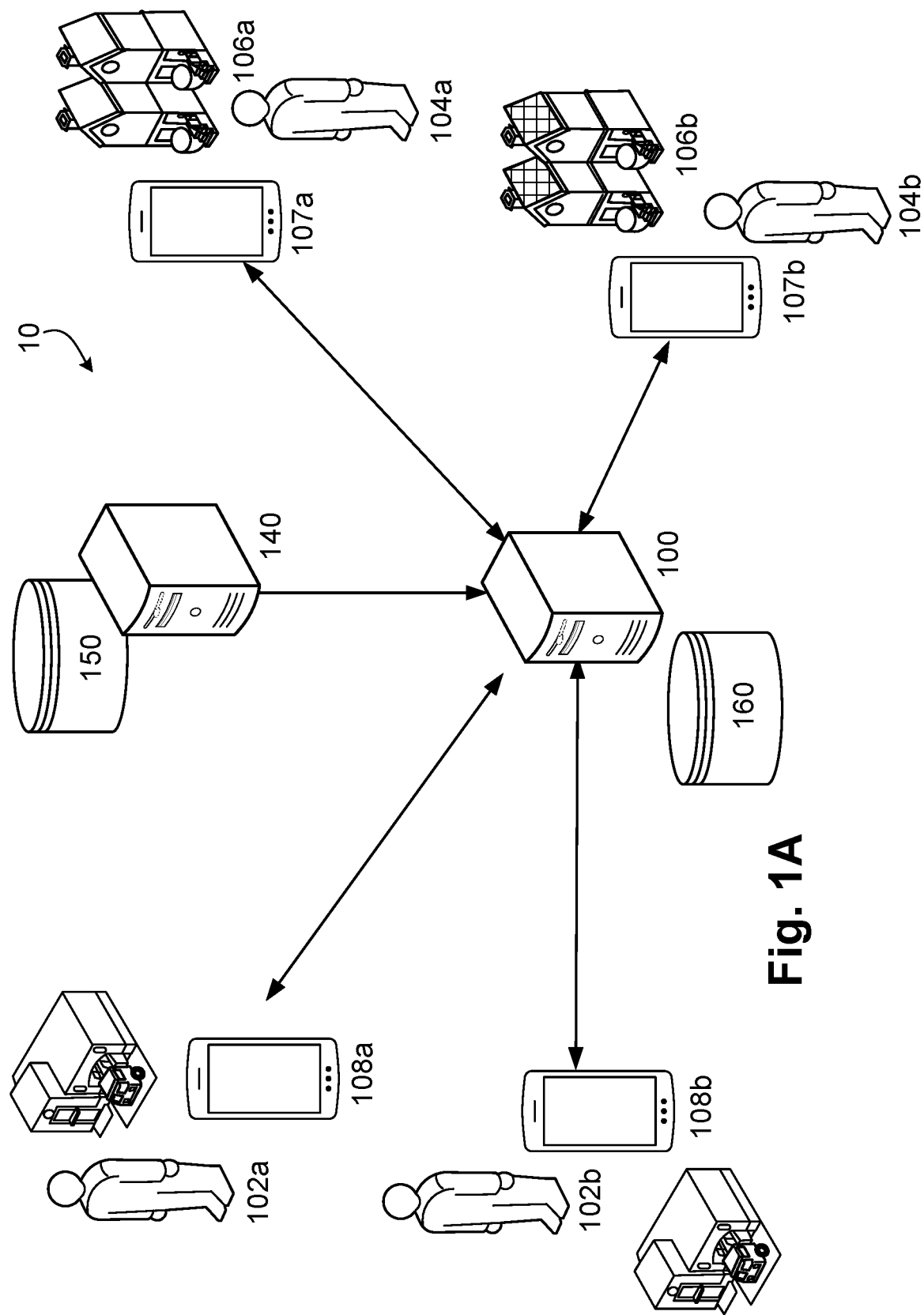
FIG. 1A is a block diagram.

FIG. 1A is a diagram showing emergency responders 102a, 102b responding to an emergency disaster situation (hereby also referred to as an "emergency situation") in a geographical area 10. The emergency situation can be a widespread disaster, e.g., a tornado, an earthquake, a hurricane, a blizzard, or another type of disaster. As a result of the emergency situation, people 104a, 104b (sometimes referred to collectively as people 104) have fled to one or more shelters 106a, 106b, respectively. We sometimes refer to the people 104 who are not acting in an emergency responder capacity as civilians. The shelters 106a, 106b (sometimes referred to collectively as shelters 106) described here can refer to private spaces (e.g., homes or businesses) or public spaces (e.g., municipally owned facilities) that have been designated as disaster relief shelters by potential victims, emergency responders, public officials, charitable organizations, or other individuals or organizations.

The emergency responders 102a, 102b (sometimes referred to collectively as emergency responders 102) can respond to the emergency situation according to information, guidance, or both, provided from a centralized computing device (e.g., a server 100. The information can be information about one or more of the shelters or the potential or actual occupants of the shelter. The information can be useful to the emergency responders 102, e.g., in determining an appropriate response to the emergency situation. The emergency responders 102a, 102b can receive information from the central server 100 on respective computing devices 108a, 108b (sometimes referred to collectively as computing devices 108). The computing devices 108 can be mobile computing devices (e.g., a mobile telephone, a tablet, a wearable computing device such as a wrist-worn computing device or computer-enabled glasses, or another type of mobile computing device), medical devices (e.g., a defibrillator, such as a professional defibrillating system or an automated external defibrillator (AED)), computing devices housed in an ambulance or other vehicle (e.g., a dispatch computing device), or another type of computing device. The computing devices 108 can display the information provided from the central server 100, such as emergency response information about the emergency situation. In some cases, the computing devices 108 can display information indicative of guidance provided from the central server, such as an emergency response plan developed by the central server 100. The emergency responders 102 can interact with the computing devices 108 via user interfaces, such as a touchscreen display, a keyboard, or another type of user interface, through interactions such as voice commands, gestures, eye movements, or another type of interaction.

The central server 100 can provide information about the shelters to the emergency responders 102. For instance, the central server 100 can provide information indicative of the location of one or more shelters 106, such as shelters in a particular region of the geographical area 10, shelters 106 known to be occupied, shelters of a particular type (e.g., public or private shelters), etc. The information indicative of the location of a shelter can include geographical coordinates, e.g., global positioning system (GPS) coordinates), an address of the shelter, a landmark near the shelter, a description of the property on which the shelter is located, or other information.

The central server 100 can provide information about the status or condition of a particular shelter, such as whether utilities such as electricity and running water are available and functional, the availability of medical supplies such as a first aid kit or an AED, or other status or condition information.

The central server 100 can provide information about the actual or potential occupants of a particular shelter 106 to the emergency responders 102. By actual occupants of a shelter, we mean people who are present in the shelter. By potential occupants of a shelter, we mean people who are expected to flee to the shelter, e.g., people who have registered with the shelter or people who live or work near the shelter. For instance, the central server 100 can provide information indicative of the number of actual or potential occupants of the shelter, an identity of at least one of the actual or potential occupants of the shelter, demographic information about the actual or potential occupants of the shelter, a medical condition of at least one of the actual or potential occupants of the shelter (e.g., an occupant with a heart condition), or a health status of at least one of the actual people in the shelter (e.g., a person who is experiencing heart palpitations or who has broken a leg).

The information provided to the emergency responders 102 by the central server 100 can be used to help the emergency responders 102 effectively provide assistance during and after the emergency situation. In some examples, the central server 100 can provide information about a set of shelters 106 responsive to a request from an emergency responder 102, e.g., a request listing the shelters 106 the emergency responder 102 has been assigned to visit. The emergency responders 102 can use the information to plan an efficient route to each of the assigned shelters and to develop a response plan based on the potential or actual occupancy of the shelter. In some examples, the central server 100 provides information about the shelters 106 to multiple emergency responders 102, and each emergency responder can select a shelter to handle. In some examples, the central server 100 can provide additional information that can help the emergency responders 102, such as directions to a shelter, information about impassable roads, information about the area near a particular shelter (e.g., information about building stability in the area, civil unrest in the area), or other information.

In some examples, the central server 100 can plot a route for a particular emergency responder 102 based on the list of shelters assigned to the emergency responder. For instance, the central server 100 can instruct an emergency responder 102a to visit a particular shelter 106b, and provide responder 102a with one or more routes to get to the shelter 106b from a given location. The given location, for example, can be the current location of the responder 102a. In another example, the central server 100 can identify a particular emergency responder 102 to respond to a particular shelter 106, e.g., based on the emergency responder's location relative to the shelter, the medical equipment carried by the emergency responder, the emergency responder's expertise, or other factors.

In some examples, some information about the shelters 106 can be obtained by the central server 100 prior to the emergency situation, e.g., by obtaining, aggregating, processing, and storing information from public sources or from private sources to which the central server 100 can obtain access. For example, a shelter registry 150, (e.g., a public shelter registry hosted at a server 140, such as a server administered by a municipality or a non-profit organization), can store information about pre-registered shelters 106, such as information indicative of the location of one or more shelters 106, medical equipment (e.g., AEDs) available at each shelter, shelter characteristics, such as a listing of facilities or amenities available at a shelter (e.g., a bathroom, a kitchen, electricity, running water, air conditioning, or other facilities or amenities), a prediction of the duration of time that the shelter can sustain its occupants in the event of a widespread disaster, or other information. In some examples, the shelter registry 150 can store information about potential occupants of a particular shelter, such as the identity of a potential occupant, health conditions or demographic information of the potential occupant, or other information. A person 104 can register with the shelter registry 150, e.g., through a web-based data entry service or through an application (which we sometimes call an "app") executable on a mobile computing device (described in more detail below).

In some examples, the central server 100 can obtain information contained in the shelter registry 150 and store the information in a database 160. For instance, the central server 100 can periodically (e.g., once per day, once per week, once per month, or with another frequency) poll the shelter registry 150 to obtain updated shelter information. In some examples, the central server 100 can access the shelter registry 150 in real time during an emergency situation and update information in the database 160 as the emergency situation evolves.

During the emergency situation, the central server 100 can obtain updated information about the shelters 106 based on input from one or more people 104, input from one or more emergency responders 102, or information from remote sources (e.g. public servers, business-provided databases, or other sources). In some examples, a person 104 can provide information about the occupants of a shelter to the central server 100. For instance, one or more of the people 104a, 104b may be equipped with a respective computing device 107a, 107b (e.g., a mobile telephone, a tablet, a wearable computing device such as a smart watch or glasses, or another type of mobile device) that the person 104 can use to report status information to the central server 100, such as an identifier (e.g., a name or location) of the shelter 106, the total number of people 104 in the shelter 106, the age of the people 104 in the shelter 106, the person's health status or the health status of other people 104 in the shelter 106 (e.g., whether he/she or another person is experiencing chest pain or breathing difficulties, whether he/she or another person is injured, or another type of health status), the status of the shelter 106 (e.g., whether the shelter 106 has electricity, whether the shelter 106 has a working AED or other medical equipment, whether the shelter 106 is in need of supplies, such as food, water, medical supplies, or other supplies), or other status information.

In some examples, an emergency responder 102 can provide information about the status of a shelter 106 visited by the emergency responder 102 during the emergency situation. For example, the emergency responder 102, upon visiting the shelter 106, can report that the people 104 at the shelter are in stable condition. In other implementations, a shelter can be equipped with sensors, e.g. occupancy sensors, that can detect a number of people 104 in the shelter and relay information indicative of the number of occupants to the central server 100, e.g., through a wireless Internet connection, a cellular network connection, a radio connection, or another type of connection. For instance, an Internet-connected household appliance, such as an Internet-connected thermostat can act as an occupancy sensor.

In some examples, the central server 100 can collect information regarding road closures or conditions, e.g., as a continuous stream of data from a source of road information or by periodically (e.g., once every half hour, once an hour, twice per day, once per day, once per week, or with another frequency) polling a source of road information. This information regarding road closures or conditions can be provided to the emergency responders 102 or can be used by the central server 100 to determine a best route for an emergency responder 102 to take to a shelter 106. In some examples, the central server 100 can collect information about facilities and equipment available for disaster relief and response, such as grocery stores, hospitals, and hardware stores.

In some examples, emergency responders 102 can register or be registered (e.g., by an employer) with the central server 100, e.g., to provide information about their expertise, years of experience, or other information.

Figure 1B:
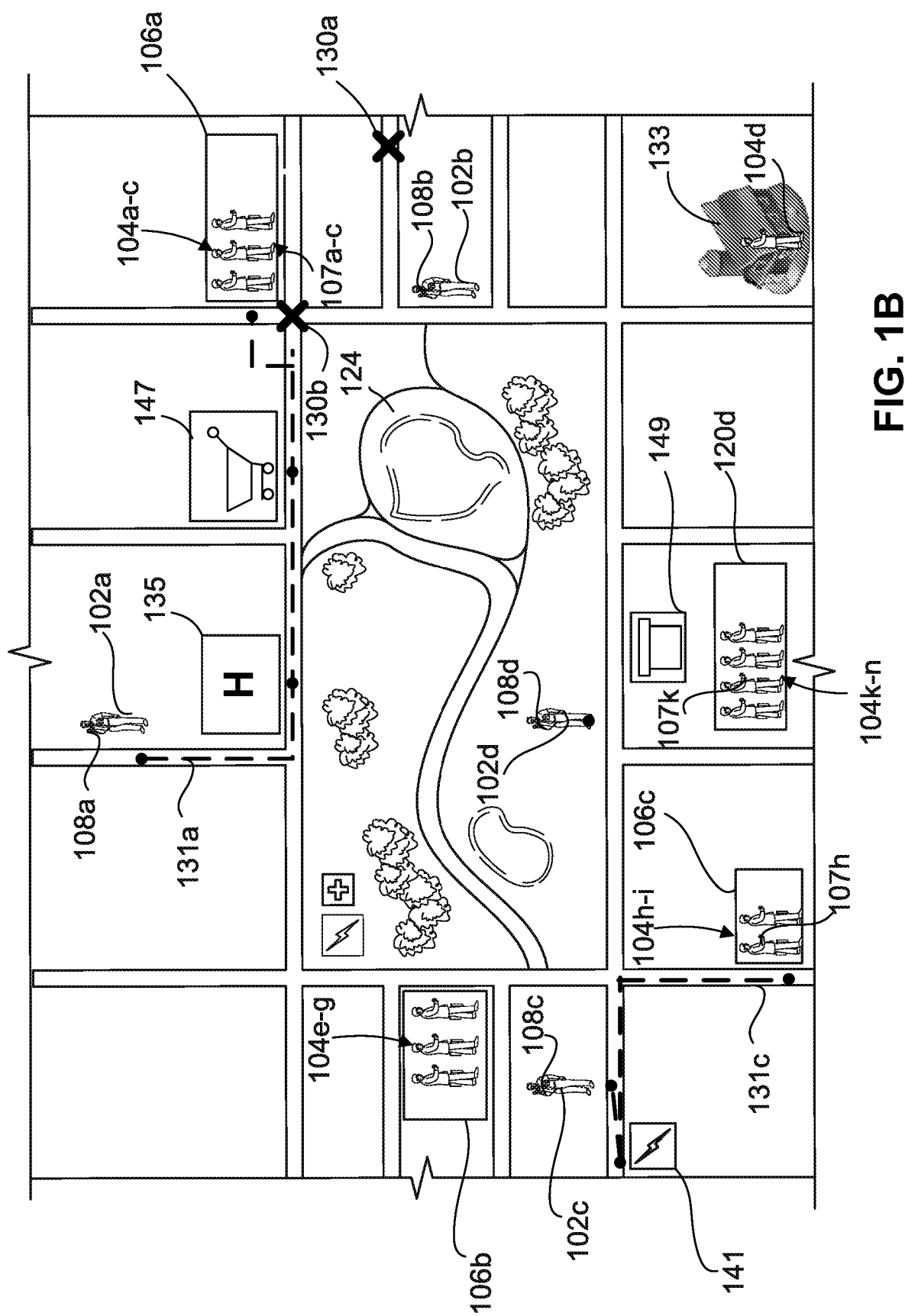
FIG. 1B is a conceptual diagram showing an emergency response.

FIG. 1B describes a specific example in which a hurricane has struck the geographic area 10. Prior to the hurricane, four emergency responders 102a-d were registered in the central server 100 with information such as expertise, duration of experience, language fluency, etc. Information related to a hospital 135 and a grocery store 147 is also registered with the central server 100. Prior to the hurricane, the hospital 135 indicated that medical supplies, including defibrillators, first aid kits, and medications, would be available in a disaster situation. The grocery store 147 also indicated that it will make available food and water amenities in a disaster situation. Other resources that were registered with the central server 100 include an AED 141 and a hardware store 149.

Shelters 106a-c were registered in a public shelter registry 150. People 104a-c were registered as potential occupants of the shelter 106a, people 104d-f were registered as potential occupants of the shelter 106b, and people 104g-i were registered as potential occupants of the shelter 106c. Some of the people provided personal information, such as identifying information, demographic information, or medical information, for storage in the public shelter registry 150. People 104j-n and the shelter 106d were not registered in the public shelter registry 150.

Tables 1 and 2 show example information provided to the public shelter registry 150, e.g., upon registration of a shelter or of a person. In particular, Table 1 shows example information that can be associated with the registered people 104a-i. While the information in Table 1 includes a name, associated shelter, and medical notes for each person 104a-i, other information can be included, such as demographic data, languages spoken, occupation, or other information. Table 2 shows example information that can be associated with the registered shelters 106a-c. While the information in Table 2 includes shelter location, potential shelter occupants, and amenities for each shelter, other information can be included, such as shelter conditions, nearby landmarks, or other information.

TABLE 1

Information about registered people

| Reference Number | Name | Associated Shelter | Medical Notes |
| --- | --- | --- | --- |
| 104a | Lloyd Botwright | 106a | Type 1 Diabetes |
| 104b | Aaron May | 106a | >90 years of age |
| 104c | Manny Penzig | 106a | |
| 104d | Shelton Olhouser | 106b | |
| 104e | Ning Jin Ruan | 106b | |
| 104f | Berthold Lange | 106b | |
| 104g | Ashok Singh | 106c | |
| 104h | Mukesh Jain | 106c | |
| 104i | Luigi Rovigatti | 106c | History of heart failure |

TABLE 2

Registered shelter information

| Reference Number | Location | Potential Occupants | Amenities |
| --- | --- | --- | --- |
| 106a | Latitude: 41.658549° Longitude: −70.392151° | Lloyd Botwright Erin May Manny Penzig | No food. No medical supplies. One gallon of potable water. No running water. |
| 106b | Latitude: 41.658325° Longitude: −70.394468° | Jane Olhouser Ning Jin Ruan Berthold Lange | Three days of food. Basic first aid supplies. Fifteen gallons of potable water. Bathroom and running water. |
| 106c | Latitude: 41.657171° Longitude: −70.393267° | Ashok Singh Mukesh Jain Alicia Rovigatti | No food. First aid supplies and AED. Ten gallons of potable water. No running water. |

Upon landfall of the hurricane, people 104a-c have fled to the shelter 106a, people 104e-g have fled to the shelter 106b, people 104h-i have fled to the shelter 106c, and people 104k-n have fled to the shelter 106d. The person 104d has taken refuge in a barn 133, which is not registered with the shelter registry.

The shelter 106a, which, prior to the hurricane, had a functional wireless Internet connection with the central server 100, is no longer in communication with the central server. The occupants of the shelter (people 104a-c) are equipped with computing devices 107a-c but are unable to communicate with the central server. As a result, no updated information about the shelter 106a or its occupants can be provided to the central server 100.

The shelter 106b has maintained communication to the central server via a wireless Internet connection. An occupant of the shelter 106b (e.g. person 104e), sends an update to the central server indicating that people 104e-g are present at the shelter 106b, via, for example, Internet-based instant messaging, telephonic communication, or another mode of electronic communication. The person 104e also sends an update to the central server indicating that substantial supplies of food and water are available at the shelter 106b. The central server 100 updates the database 160 (FIG. 1A) to indicate the actual occupancy of the shelter 106b. The central server 100 updates the database 160 to include the food and water supplies reported by the person 104e.

The shelter 106c has lost wireless Internet communication with the central server 100. However, the person 104h has a functional mobile device 107h that can communicate with the central server 100. The person 104h sends an update to the central server using the mobile device 107h to indicate that people 104h-i are present at the shelter 106c. The person 104h also sends an update to the central server 100 indicating that the person 104i is experiencing chest pain. The central server 100 updates the database 160 (FIG. 1A) to indicate the actual occupancy of the shelter 106c and the medical condition (chest pain) experienced by an occupant of the shelter.

The shelter 106d does not have a functional wireless Internet connection with the central server. Furthermore, the person 104k has a mobile device 107k that is unable to connect to the Internet. However, the mobile device 107k can communicate with the mobile device 108d carried by the nearby emergency responder 102d through a short-distance wireless communication protocol (e.g., Bluetooth™ communications). The person 104k communicates to the emergency responder 102d, via the Bluetooth™ connection between their mobile devices 107k and 108d, that people 104k-n are present at the shelter 106d. The mobile device 107k has a GPS receiver that indicates the approximate location of the mobile device 107k. As a result, the person's mobile device 107k also transmits approximate location information of the shelter 106d (and the people 104k-n) to the mobile device 108d of the emergency responder 102d. When the emergency responder's mobile device 108d establishes communication with the central server 100, the information provided by the person 104k can be transmitted to the central server. The central server 100 updates the database 160 (FIG. 1A) to indicate the actual occupancy of the shelter 106d.

In the example of FIG. 1B, the central server 100 uses the shelter registry and the updated information provided by people in the shelters to instruct the emergency responders 102 in responding to the emergency situation. For instance, based on information in the shelter registry, updated information provided by people in the shelters, or both, the central server 100 determines that shelters 106a and 106c are high priority for emergency assistance. Based on information about each of the high priority shelters 106a, 106c and based on information about the emergency responders 102 and their locations, the central server 100 determines a highest priority shelter for each emergency responder 102a-c and a route for each emergency responder 102a-c to move from his/her current location to the corresponding highest priority shelter. The priority of a shelter for a particular emergency responder 102a-c can depend on factors such as the distance from an emergency responder 102a-c to the shelter, the expertise of the emergency responders 102a-c, or environmental conditions (e.g., road or building conditions at or near the shelter, resources available near the shelter).

For instance, in the example of FIG. 1B, the emergency responder 102b has been assigned the shelter 106b as his/her highest priority shelter. Although the emergency responder 102b is closer to the shelter 106a than to his/her assigned shelter 106b, the central server 100 has received information regarding road closures 130a-b blocking the route from the emergency responder's current location to the shelter 106a. Accordingly, the central server 100 determines that the emergency responder 102b can more quickly access the shelter 106b. The emergency responder 102a has been assigned the shelter 106a as his/her highest priority shelter and the emergency responder 102c has been assigned the shelter 106c.

In assigning the emergency responder 102a to the shelter 106a, the central server 100 has also taken into account that the emergency responder 102a is near the hospital 135, where he can pick up vital medications and equipment for the potential occupants 104a-c of the shelter 106a that include a diabetic and an ill elderly person. The central server 100 sends, to the mobile device 108a of the emergency responder 102a, information indicative of the status of the potential occupants of the shelter 106a, given that the occupancy of the shelter is unknown. The central server also sends, to the mobile device 108a, information indicating that a potential occupant of the shelter 106a may require medical attention due to potential complications with diabetes, that another potential occupant may require medical attention due to maladies related to age, and that the shelter 106a is not prepared with amenities (e.g. food and water) to sustain three people for more than a few hours. The central server 100 also sends instructions to the mobile device 108a indicative of a route 131a to be taken by the emergency responder 102a to arrive at the shelter 106a. The route 131a accounts for road closures 130a-b caused by hurricane debris. The route 131a includes a stop at the hospital 135 to collect insulin for the potential occupant 104a and a first aid kit for general medical care of the shelter occupants 104a-c. The route 131a also includes a stop at the grocery store 147 to gather water and food for the potential occupants of the shelter 106a. As the emergency responder 102a follows the route 131a according to instructions from the mobile device 108a (which receives the instructions from the central server 100), the mobile device 108a can relay other information about the potential occupants 104a-c of the shelter 106a, such as names and languages spoken.

The shelter 106c has an occupant whose primary language is Flemish. The database 160 administered by the central server 100 indicates that the emergency responder 102c is fluent in English and Flemish. The mobile device 108c directs the emergency responder 102c to navigate the route 131c first to an AED 141 (represented by a thunderbolt symbol) and then to the shelter 106c, where the shelter occupants 104h-i are awaiting aid. The central server 100 has determined that the shelter 106c requires immediate assistance due to the chest pains experienced by the person 104i. In assigning an emergency responder 102 to the shelter 106c, the central server 100 considered the location of assistive medical devices, such as the AED 141, that can possibly be used to treat the person 104i. The emergency responder 102c is closest to the AED 141. Thus, given both the proximity of the emergency responder 102c to the AED 141 and the emergency responder's fluency in Flemish, the central server assigns the emergency responder 102c to the shelter 106c. The central server 100 sends, to the mobile device 108c of the emergency responder 102c, instructions indicative of a route 131c to be taken by the emergency responder to arrive at the shelter 106c, including a stop at the AED 141. The central server 100 also sends information indicating that two people are present in the shelter, one of whom is experiencing chest pain.

Figure 2A:
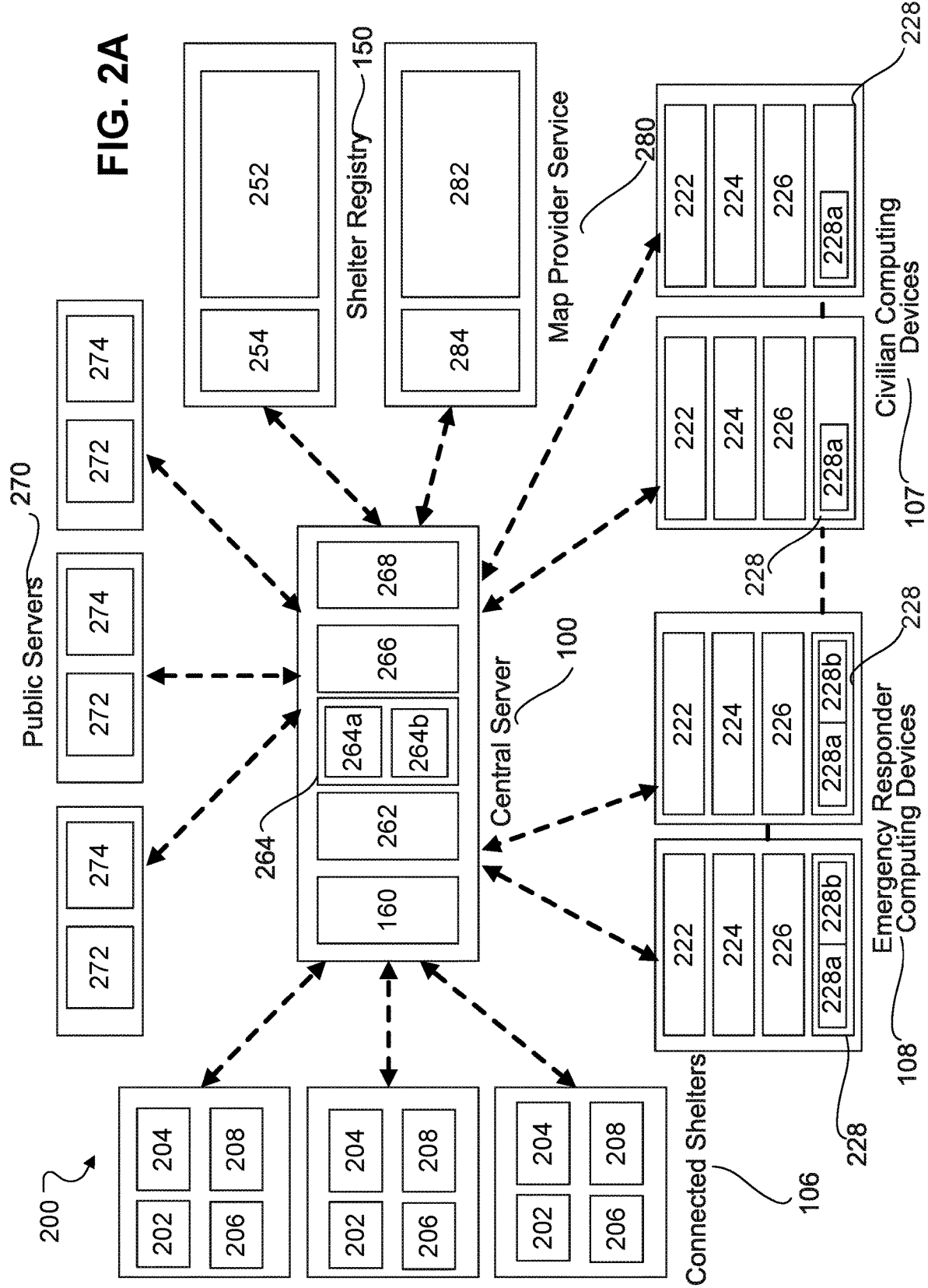
FIGS. 2A and 2B are example node diagrams.
Figure 2B:
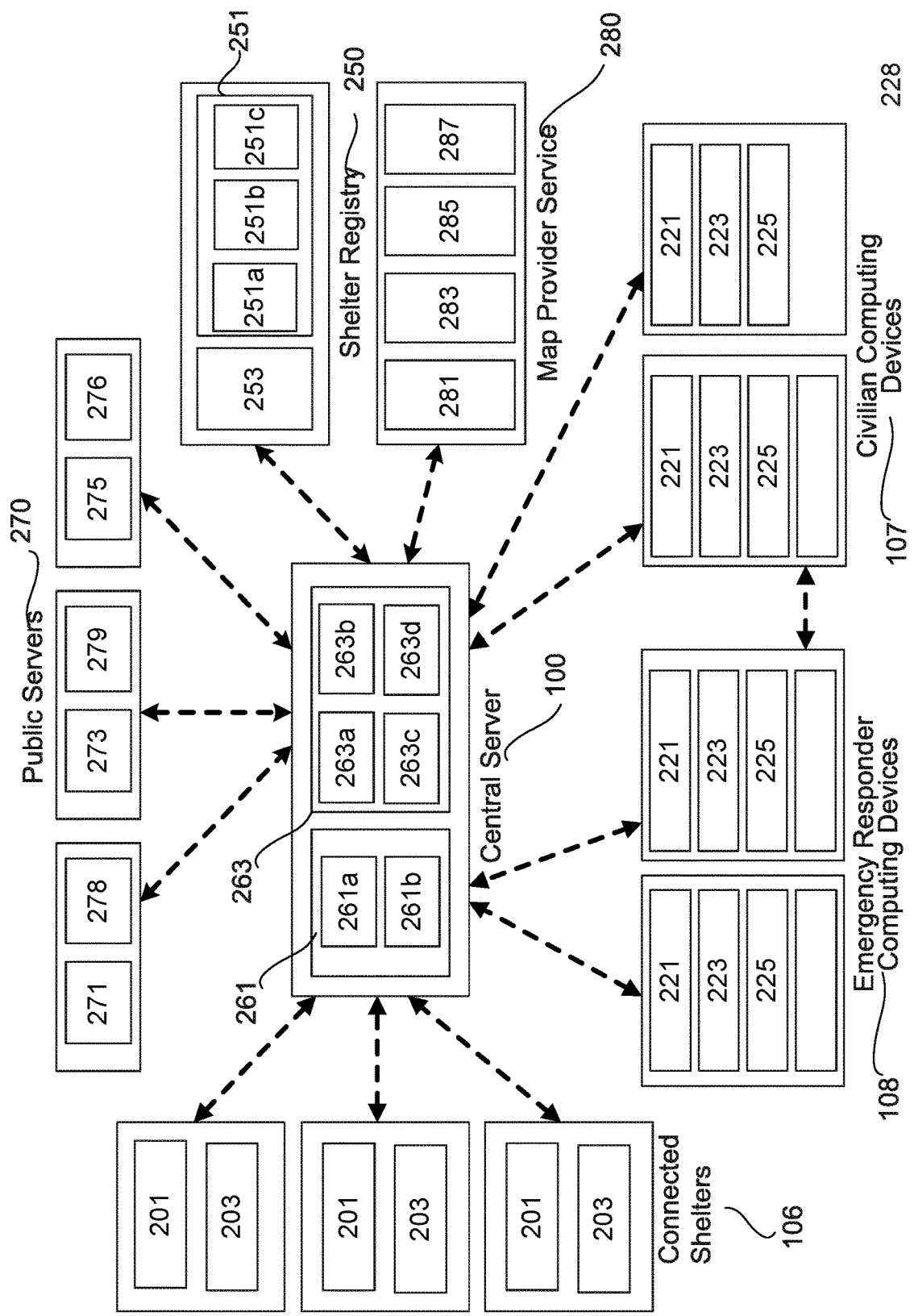

FIGS. 2A-B are block diagrams that depict example nodes of a system 200 for assisting with an emergency response to an emergency situation. FIG. 2A is a block diagram of the system 200 that includes nodes (for example, central server 100, public servers 270, connected shelter 106, emergency responder computing device 108, civilian computing device 107, map provider service 280, shelter registry 150 etc.) and sub-systems of each node. FIG. 2B is a block diagram of information stored by a node or transmitted among nodes. By nodes, we mean computing devices (e.g., servers, databases, mobile computing devices, or other types of computing devices) that form part of the system 200. By way of general overview, the system 200 includes the central server 100, which communicates with other nodes in FIG. 2A, including the shelter registry 150, the connected shelters 106, public servers 270, emergency responder computing devices 108, computing devices 107 associated with people 104, and a map provider 280. Each node can communicate with one or more other nodes, e.g., as shown by unidirectional arrows (indicating information flow in one direction) or bidirectional arrows (indicating information flow in both directions).

In some examples, the nodes in the system 200 can be communicably coupled through wireless communication systems. In some examples, the nodes can be coupled to form networks through electrical coupling by, for example, a wire; optical coupling by, for example, an optical cable; and/or other wireless coupling by, for example, a radio frequency or other transmission media. The network can include one or more networks. The network(s) may provide for communications under various modes or protocols, such as Global System for Mobile communication (GSM) voice calls, Short Message Service (SMS), Enhanced Messaging Service (EMS), or Multimedia Messaging Service (MMS) messaging, Code Division Multiple Access (CDMA), Time Division Multiple Access (TDMA), Personal Digital Cellular (PDC), Wideband Code Division Multiple Access (WCDMA), CDMA2000, General Packet Radio System (GPRS), or one or more television or cable networks, among others. For example, the communication may occur through a radio-frequency transceiver. In addition, short-range communication may occur, such as using a BLUETOOTH™, WiFi, short wave radio, very high frequency (VH) radio, short wave modems, or other types of short-range communication. In some cases, other types of communication can be used, such as FAX over radio.

In some examples, basic shelter information, such as shelter location or shelter occupancy, can be broadcast using a beacon application through a low power broadcast protocol, such as a wireless (e.g., WiFi) or Bluetooth™ connection. To guide a rescuer to a shelter, a higher power beacon, such as a personal locator beacon (e.g., an Emergency Position-Indicating Radio Beacon (EPIRB), can be used. In some examples, shelter location information can be broadcast over very high frequency (VHF) and satellite radio frequencies, e.g., using Marine Automatic Identification System (AIS) Man Overboard (MOB) devices. Information about personal locator beacons (PLBs), such as beacons for marine use or use on land, can be included in the shelter registry 150.

Referring to FIG. 2A, the central server 100 includes the database 160, a central processor 262, a wireless communication system 264, a dispatch system 266, and a search system 268. The central server 100 causes information about, for example, emergency responders, shelter occupants, shelters, available resources, environmental conditions, or other information to be stored in the database 160. Information stored in the database 160 can include information acquired prior to a disaster event and during a disaster event. The central server 100 can manage the receipt and delivery of the information from and to other nodes through its wireless communication system 264. The wireless communication system 264 includes a responder communication sub-system 264a to directly communicate with emergency responders and a civilian communication sub-system 264b to facilitate communication directly with civilians. In some examples, one or both of the sub-systems 264a, 264b can be used to transmit a widespread alert to both civilian computing devices 107 and emergency responder computing devices 108, such as a tornado warning. In some examples, one or both of the sub-systems 264a, 264b can be used to transmit an alert to one or more specific people, such as an alert to occupants of a particular shelter indicating that an emergency responder is on the way.

The central processor 262 of the central server 100 processes information, including, e.g., one or more of receiving, delivering, or storing information. The central processor 262 uses information about shelters or shelter occupants or other information to provide guidance to emergency responders in responding to the emergency situation. For instance, the central processor 262 can process information from the database 160 to determine a route for an emergency responder to take to a shelter. The central processor 262 can identify high priority shelters, e.g., based on information about the shelters or shelter occupants or both.

The dispatch system 266 can receive information about shelters, occupants, or both, and process the received information into a form useful to the central processor in determining emergency response guidance. The dispatch system 266 can be managed by human dispatchers who can communicate with other nodes via the wireless communication system 264. The dispatch system 266 can include an automated aspect that can process information received from people or emergency responders. For example, the dispatch system 266 can receive information about the status of a shelter occupant delivered via a text message from a person to the wireless communication systems 264. The dispatch system 266 performs an analysis of the text message (e.g., through natural language processing) and updates the status of occupant in the database 160. The dispatchers can manage phone calls from people, such as shelter occupants, and enter information into the database 160 that was collected during the phone calls. The dispatchers can inform emergency responders of complex updates to routes, emergency incidents, the emergency situation, or shelters. A dispatcher may speak to a person via the civilian communication sub-system 264b to find out that the person is having a heart attack at a particular location. The dispatcher may enter the information about the call into the database 160, and the processor 262 can use the information from the call, e.g., in determining rescue priorities for the emergency responders. In some examples, the dispatcher can collect complex instructions, e.g. provided through the civilian communication sub-system 264b, to find and enter a well-hidden shelter. The dispatcher can then relay this information via the responder communication sub-system 264a to the emergency responders' mobile devices 108.

The central server 100 can include the search system 268, which searches through the public servers 270 to gather publicly available information. The search system 268 identifies emergency response information by crawling and indexing information provided by the content publishers on websites of, for example, the public servers 270. The data can be indexed based on the emergency response information to which the data corresponds. Indexed and, optionally, cached copies of the emergency response information that match input keywords can be retrieved and output, e.g., in response to a search query. For example, the search system 268 can find public social media posts that can indicate the status of particular shelter occupants. The search system 268 can also determine, for example, weather and environmental conditions based on publicly available information.

The central server 100 can provide information to other recipients. For example, the central server 100 can inform local hospitals of the number of victims that the hospitals are likely to receive, and the approximate time until the victims will arrive. In some examples, emergency responders or other recipients of information from the central server may choose to filter communications so that they see or hear only messages that are relevant to them, e.g., using techniques such as subscriptions to "channels" having messages that are tagged with items such as "hash tags" that are used to filter communications on social networks such as TWITTER™.

One or more of the shelters 106 can be in communication with the central server 100, e.g., through wired or wireless Internet communication, cellular network communication, or another type of communication. Each connected shelter 106 can include one or more of a communication system 202, an occupancy sensing system 204, and a user interface 206. The occupancy sensing system 204 in a shelter 106 can automatically detect and transmit information about shelter occupancy, such as whether the shelter is occupied or the number of occupants detected in the shelter 106. The user interface 206 in a shelter 106 allows shelter occupants to input information and receive information. The user interface 206 can be used to engage in, for example, text-based or video-based communication with the central server 100 or other computing devices. The user interfaces 206 can also be used to store information in data storage elements 208, e.g., to store information input by a shelter occupant until the communication system 202 establishes communication with the central server 100. For example, the data storage element 208 can contain a stored broadcast that is emitted through a radio transceiver of the wireless communication systems 202. The radio transceiver can regularly emit signals corresponding to the stored broadcast.

Referring also to FIG. 2B, the communication system 202 in a shelter 106 can be used to transmit occupant data 201 or shelter condition data 203 or both to the central server 100. The data can be collected automatically, e.g., by the occupancy sensing system 204, or can be input by a shelter occupant or by an emergency responder. Occupant data 201 can include, e.g., an indication of whether the shelter is occupied, a number of occupants, a status of the occupants, or other information. Shelter condition data 203 can include, e.g., an amount of food or water available, an estimated amount of time that the occupants can survive in the shelter without assistance, a physical or structural condition of the shelter, or other information.

The shelter registry 150 includes a shelter database 252 and a communication system 254, such as a wired or wireless Internet communication system, a cellular network communication system, or another type of communication system. The communication system 254 allows direct communication with computing devices 107, 108 as well as communication with the central server 100. The shelter database 252 stores shelter data 251 and occupant data 253. In some examples, shelter data 251, occupant data 253, or both can be provided by a person, e.g., when registering a shelter or when registering as a potential occupant of a shelter. In some examples, some information can be provided by the shelter itself. For instance, a connected shelter can automatically transmit its location to the shelter registry 150.

The shelter data can include shelter location data 251a, shelter amenity data 251b, or a list of potential occupants 251c, or other information. Location data 251a can include, e.g., latitude and longitude coordinates, an address, landmarks, a property description, or other data. Shelter amenity data 251b can include, e.g., an amount of stored food, water, or medical supplies; available facilities (e.g., bathrooms, running water, number of rooms, construction materials); or other information. The list of potential occupants 251c can include a number of potential occupants, an identity of one or more potential occupants, or other information about the potential occupants.

The occupant data 253 can include identity data, health information, shelter data, electronic medical record (EMR) data, or other information. Identity data can include, e.g., legal names, identification numbers such as driver's license numbers or social security numbers, or other pieces of identifying information. Health information can include, e.g., medical conditions, blood type, allergies, medications, or other information. Medical conditions can include benign or potentially life-threatening medical conditions, e.g., heart disease, diabetes, paralysis, or other medical conditions. Shelter data 251 includes identifiers of one or more shelters at which a particular person is listed as a potential occupant. Other information can include skills (e.g., CPR training or EMT training), language fluency, occupation, other information.

The map provider 280 has a map database 282 and a communication system 284, such as a wired or wireless Internet communication system, a cellular network communication system, or another type of communication system. The communication system 284 transmits map information to one or more of the central server 100, the emergency responder computing devices 108, or the civilian computing devices 107. The map provider 280 stores one or more of mapping data 281, location data 283, routing data 285, or satellite data 287, or other data. The mapping data 281 can include, e.g., visual map tiles or data that can be used to connect coordinates (e.g., latitude/longitude coordinates) to locations on the map. Location data 283, representative of locations on the map, can include the location of points of interest such as emergency facilities, pharmacies, grocery stores, supermarkets, and other facilities that may provide resources during an emergency. The routing data 285 are data used to generate navigational routes on maps. The routing data 285 can be used to convert natural language addresses to technical map identifiers such as latitude/longitude coordinates. In some examples, not all of the data 281-287 are stored on the map provider. For instance, some or all of the data 281-287 can be accessed at a remote server, such as a server provided by a third-party mapping service such as Google Maps™, e.g., using public application program interfaces (APIs).

One or more public servers 270 each includes a public database 272 and a communication system 274, such as a wired or wireless Internet communication system, a cellular network communication system, or another type of communication system. The communication systems 274 allow the central server 100 to receive information from the public databases 272. The public databases 272 can include information such as weather data 271, traffic data 278, road condition data 273, utility status data 279, social media data 276, news reports 275, or other publicly available information databases.

The emergency responder computing devices 108 and the civilian computing devices 107 can include communications systems 222, sensor systems 224, processors 226, and data systems 228. The sensor systems 224 can include GPS sensors accelerometers, heart rate sensors, and altimeters. The processors 226 can receive information and store the information on the data systems 228. The data systems 228 (e.g. data storage elements, memories, etc.) can store information, such as sensing data 221, map data 223, or software data 225. The communication systems 222 can include one or more of long-range communication sub-systems or short-range communication sub-systems. The data systems 228 may each be loaded with one or more of a disaster response application 228*a* (described below) or a map/navigation application 228*b* loaded onto the devices 107, 108. The map/navigation application 228*b* may receive location information from the sensor systems 224 and may receive maps from the map provider 280 and/or from the central server 100, such that the map/navigation application 228*b* may generate a map that may be overlaid with navigation information, and may also provide turn-by-turn navigation as an emergency responder moves toward an emergency situation.

FIG. 2B depicts emergency response information stored at each node, for example, in databases and memory storage elements of the nodes. Flow of information is depicted by unidirectional and bidirectional arrows. A unidirectional arrow indicates that flow of information goes in only one direction, whereas a bidirectional arrow indicates that information flows in both directions. As described earlier, the system 200 includes the central server 100, the shelter registry 150, the connected shelters 106, the public servers 270, the emergency responder computing devices 108, the civilian computing devices 107, and the map provider 280. The nodes within the system 200 include wireless communication systems that allow them to form one or more networks. In particular, the central server 100 can directly receive information from substantially any of the nodes.

For situations in which the systems discussed herein collect personal information about people (e.g., potential shelter occupants), the people may be provided with an opportunity to opt in/out of programs or features that may collect personal information (e.g., information about a person's preferences or a person's current location, or a person's medical information). Some data may be anonymized in one or more ways before it is stored or used, so that personally identifiable information is removed. For example, a user's identity may be anonymized. Some data can be stored according to a secure protocol, e.g., according to guidelines associated with the Health Insurance Portability and Accountability Act (HIPAA).

The central server 100 can collect the shelter data 251 and the occupant data 253 from the shelter registry 150 and store the data in its own database 160 prior to the occurrence of a disaster. The central server 100 can collect and data from one or more of the other nodes of the system 200, such as the emergency responder computing devices 108 and the civilian computing devices 107, the connected shelters 106, the map provider service 280, or the public servers 270.

The database 160 of the central server 100 can also store its own information. For example, the database 160 can include resource information 261*a* and emergency responder information 261*b*. The resource information 261*a* includes location information corresponding to the location of resources that can be made available during emergency situations, such as a grocery store, a hardware store, or a hobby store that has indicated to the central server 100 that their business will provide resources during emergency situations. The database 160 can also store the location of medical devices, such as AEDs, that are located at offices and businesses. In the event of a disaster, the central server 100 can directly communicate with businesses that have agreed to supply resources. The emergency responder information 261*b*, which is provided by or on behalf of emergency responders 102 who register information with the system 200, can include information such as responder expertise, contact information, identification, age, primary residence, experience associated with particular emergency situations, or experience with other emergency responders 102, or other information.

The database 160 can store processed information 263. After the central server 100 receives information from the other nodes in the system 200, the central server 100 can process the information and produce an emergency response plan 263*a*. For example, the emergency response plan 263*a* can include a distribution of routes to the emergency responders such that the emergency situations of the highest priority can be addressed first and efficiently. The emergency response plan 263*a* can include route data 263*b*, scheduling data 263*c*, and priority data 263*d*. The route data 263*b* are the routes for each emergency responder to respond to emergency situations. The route data 263*b* can be determined by, for example, a combination of the data 281, 283, 285, 287 collected from the map provider service 280, the road conditions data 273 received from the public servers 270, location of the shelters from the shelter data 251, and location of emergency responders from emergency responder computing device sensing data 221. In some implementations, other factors may be considered as well, such as the location of emergency incidents outside of the provided shelter data 251. While the example shown in FIG. 1B describes a single route assigned to each emergency responder 104*a*-*d*, in some implementations, the emergency responders may be assigned multiple routes from the route data 263*b*. The scheduling data 263*c* can store the sequence in which the emergency responders complete their routes to ensure that the highest priority situations are addressed first. For example, the scheduling data 263*c* for an emergency responder can include a sequence of three routes to locations corresponding to emergency incidents. The scheduling data 263*c* is generated such that the first route corresponds to the highest priority of the three emergency incidents and the last route corresponds to the lowest priority of the three emergency incidents.

The scheduling data 263*c* can be generated using the priority data 263*d*, which is a list of the emergency incidents in order of priority. The priority data 263*d* can be generated using multivariate optimization techniques, such as quasi-Newton methods and steepest descent. The variables considers can include information received from the nodes in the system 200. For example, in some implementations, medical conditions of occupants at a given shelter can increase the priority of addressing the emergency incident at the shelter. A lack of supplies, such as food or water, at a location can further increase the priority for emergency responders to respond to the emergency incident at a location.

In some examples, the central server 100 can deliver information to the shelter registry 150. For instance, a person can directly register shelter and occupant data to the central server, thus bypassing the shelter registry. In these cases, the central server can inform the shelter registry of the registration. The central server and the shelter registry can periodically sync their databases such that duplicate registrations are deleted. Likewise, in some examples the central server can deliver information to the public servers. For example, the central server can broadcast messages to public news outlets informing them of the ongoing emergency response. The central server can also inform municipalities of additional city issues, such as road closures or damage that emergency responders encounter during the emergency response.

Figure 3B:
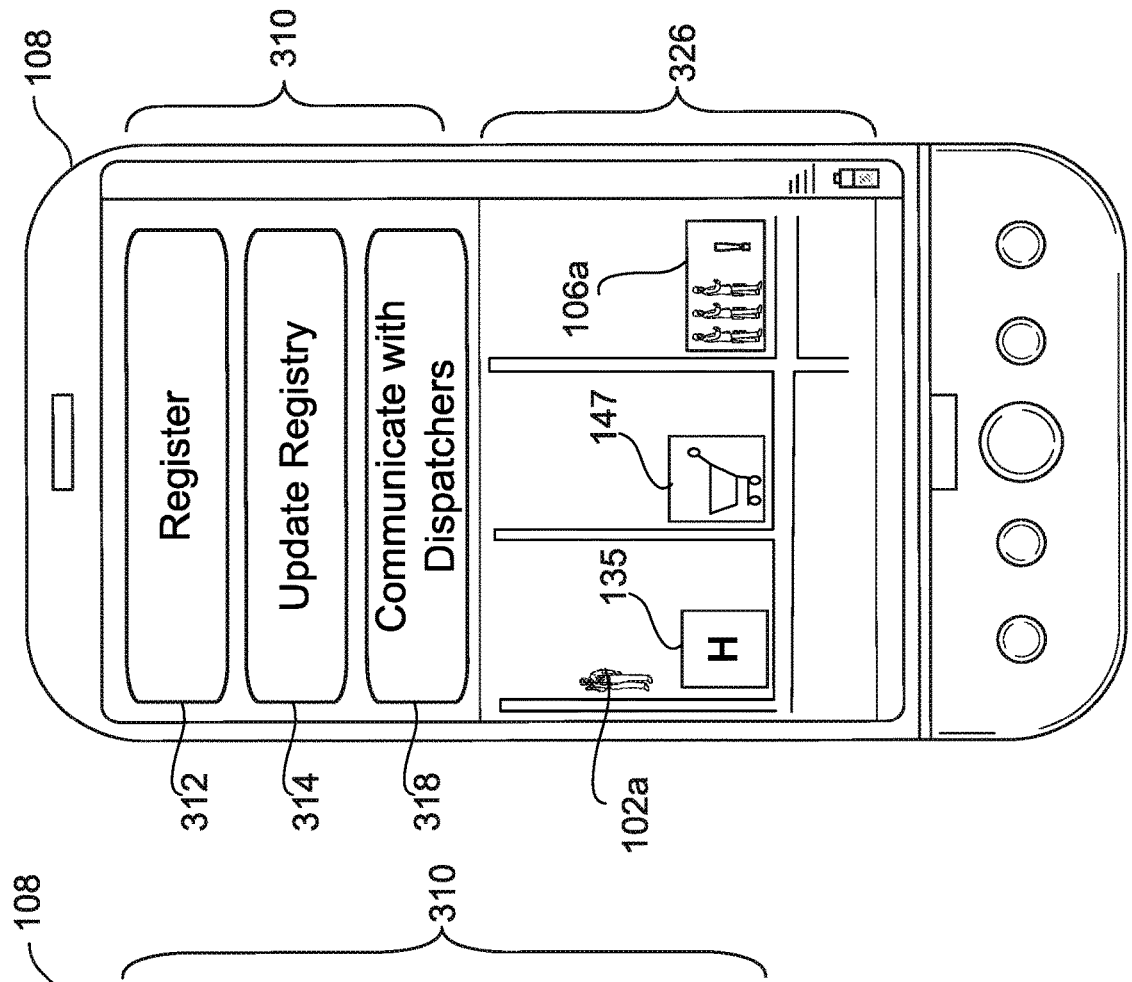
FIGS. 3A-3C are example screenshots.
Figure 3A:
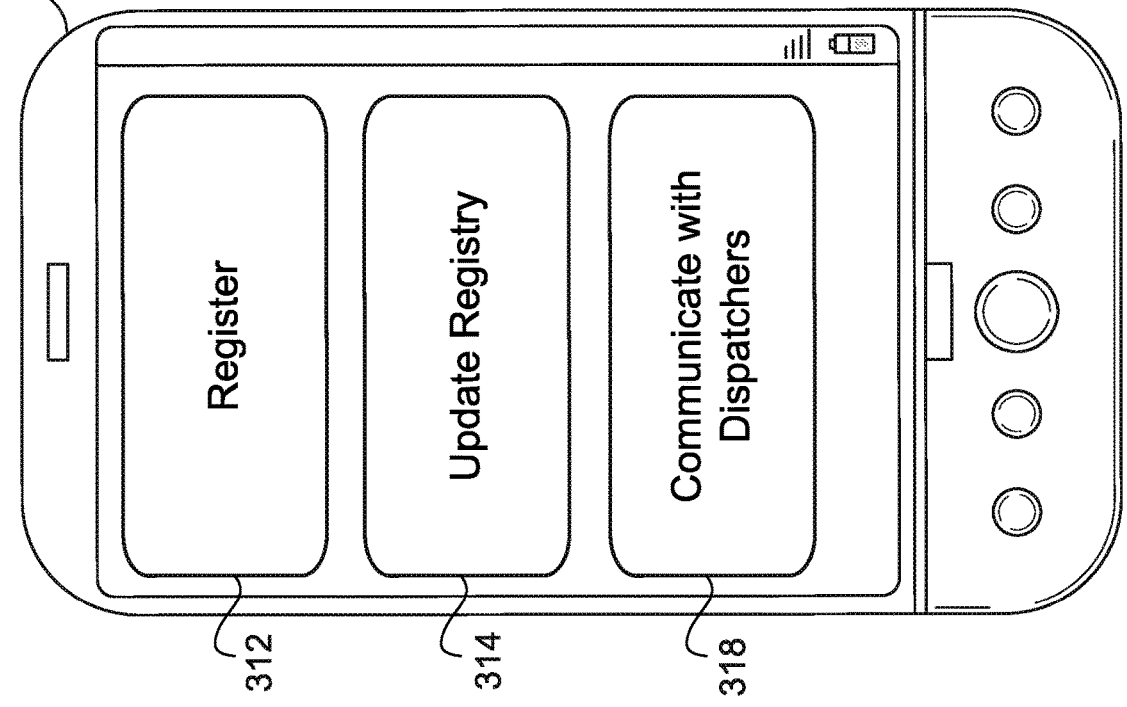
Figure 3C:
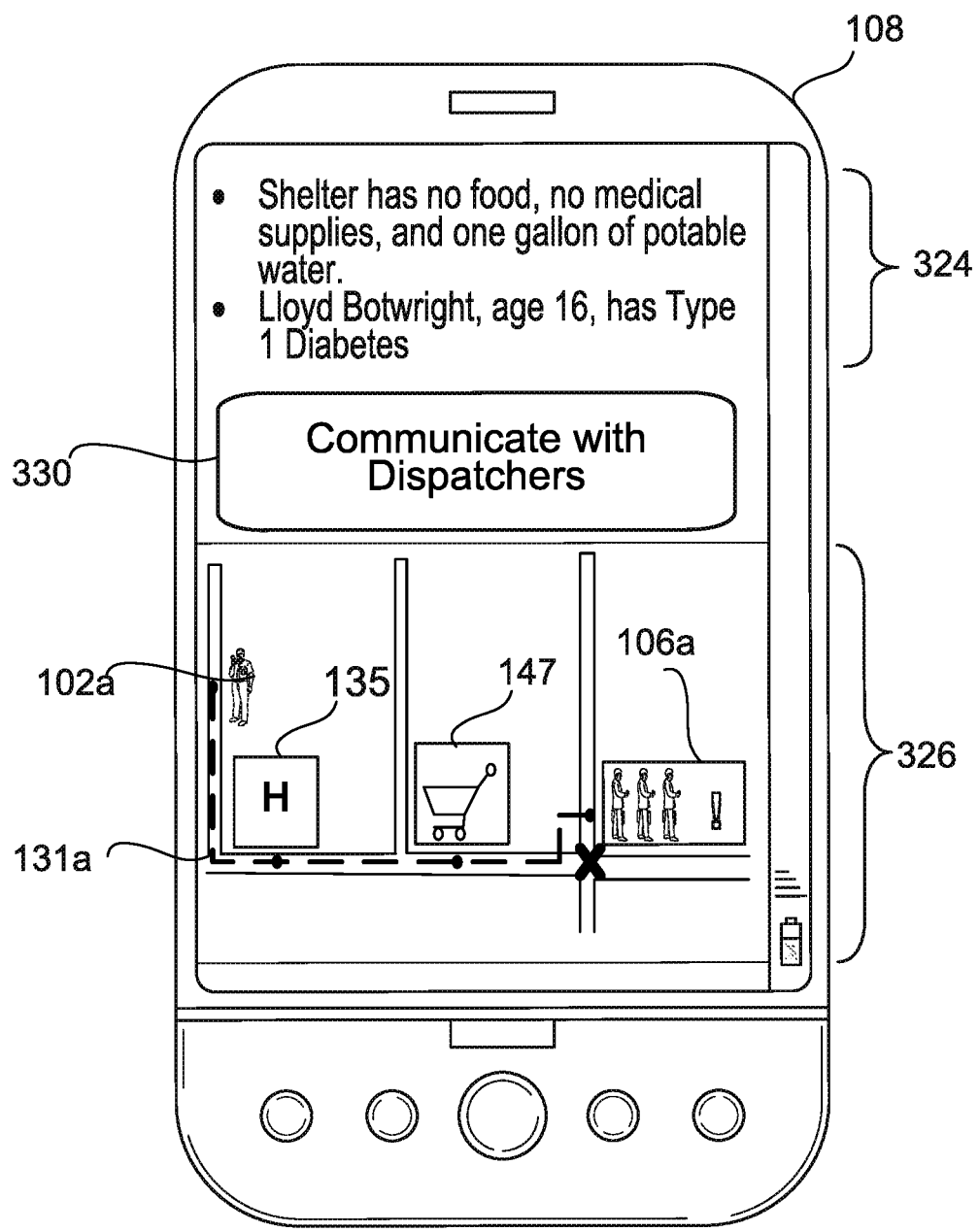

An emergency response app can be installed on a computing device 108 operated by an emergency responder 102, a computing device 107 operated by a person 104 (e.g., a potential shelter occupant), or both. In this description, we sometimes refer generally to a person who accesses the app as a user of the app. The app can include a basic user module for use by a non-responder and an emergency responder module for use by an emergency responder. In some examples, the app can be enabled to run with only one module (e.g., only the basic user module). In some examples, the app can be enabled to run with both modules. FIGS. 3A-B are screenshots of an example app with the basic user module, and FIG. 3C is a screenshot of an example app with both the basic user module and the emergency responder module. The app can prompt a user to enter certain information. The app can present questions with multiple choice answers that are straightforward for a user to answer even in a stressful situation. The application may include settings that allow for push notifications from the central server 100 and allow for the computing devices to automatically transmit information (e.g. location data). While FIGS. 3A-C depict smartphones as the computing devices, other communication devices may also be employed. For example, a user may have only a basic cellular telephone, and they may communicate by way of text messaging.

The mobile devices (e.g., emergency responder computing devices 108 or civilian computing devices 107) executing the app can directly communicate with the central server 100. In the event that communication with the central server 100 has been severed, the mobile device can utilize its personal area networks (PAN) capabilities to directly communicate with other mobile devices, and vice versa. The app may report the user's current location, e.g., as measured from global positioning system (GPS) sensors or based on WiFi network accessibility. A general location for the user can be obtained by the central server 100 by using cell tower triangulation or similar services, such as the GOOGLE MY LOCATION™ service.

FIG. 3A shows a screenshot of the basic user module prior to an emergency situation. Referring to FIG. 3A, when the central server has not declared an emergency situation, a main menu 310 includes the following options: "Register" 312 or "Update Registry Information" 314. When a user selects the register button 312, the user enters a registration portal, where the user can register the mobile device, personal information, or a shelter, e.g., by providing information such as the information described above. The entered information is delivered to the central server. Selecting the update registry information button 314 allows the user to update information that he or she has registered to the central server. In some implementations, registration can involve selecting a user name and/or a password. In some implementations, an identifier, such as a universally unique identifier (uuid) is assigned to each person or shelter upon registration.

Referring to FIG. 3B, during an emergency incident, the app user interface changes to an emergency mode. The basic user module during an emergency includes a map 326 indicating the location of nearby emergency responders (e.g. emergency responder 102a). The particular zoom level that is initially presented to the user may be selected automatically by the system. The map 326 can also include icons representing resources, e.g., a hospital icon 135 and a grocery store icon 147. The main menu can includes an option to "Communicate with Dispatchers." Selecting the communication button 318 allows users to directly communicate with dispatchers of the central server, who can in turn direct communication directly to emergency responders. In some examples, the basic user module can include an ability for a user to communicate directly to another user or emergency responder. The basic user module may have a feature allowing the user to communicate updates to the central server, provided that the central server has indicated that a disaster situation is occurring.

In certain situations, the person's mobile device may be used to provide EMR-related information about the person to rescuers. For example, users of mobile devices may input information to their device about their blood type, allergies, medications, and other relevant information (e.g., if they have hepatitis or diabetes). Users may provide this information prior to or during a disaster. Such information may then act as a form of electronic med-alert bracelet. The device may also filter the data, such as by showing limited information (e.g., blood type and a person to contact when there is an emergency) on a home screen when the device is locked, and show all the information when unlocked In addition, a patient's medical information may be stored on an amulet or other article that the person may wear (such as by using radio frequency identification (RFID) technology), and the information may be read by a standard smartphone of a rescuer, such as by using near-field communication techniques. The information, when stored electronically in any of these ways, can be transferred automatically to an electronic device of a rescuer, such as a tablet computer for an EMT, and may be saved, transferred (e.g., to a target hospital), and used in the treatment of the person.

A person may provide basic medical record information to a publicly-accessible service (for example, public servers 270), and the information may be indexed in an appropriate manner so that it can be retrieved on-site by an emergency responder. For instance, the person may be provided with a med-alert label for his or her smartphone, and may write an index number on the label that a rescuer can submit to the service in order to get the person's information. Such an index number may also be the telephone number of the person's mobile telephone, and that number may be displayed on a locked home screen of the telephone.

In some examples, the user module can include a messages section that allows the central server 100 to communicate to users in a non-disaster situation. For example, the central server can communicate warnings of potential disasters or notify users of potential ways to prepare for disaster situations. In some implementations, the mobile devices of the users will have "push notifications" activated, and the central server can notify the users through the push notifications system of recommendations to be prepared for disasters. The central server can send out periodic newsletters with checklists and tips for disaster preparation.

In some examples, prior to an emergency situation, the user module can enable periodic transfers of information from the computing/mobile devices 107, 108 to the central server 100 in order to preempt potential communication rifts between the mobile device and the central server in the event of a disaster. The mobile device can periodically send its location, so that if a disaster occurs and destroys communication means, the central server will have historical location information and be able to predict where the user might be.

For the responder module, additional functionality allowing emergency responders to execute an efficient emergency response and rescue is provided through the app. Referring back to FIG. 1B, the map shows an iconic representation of resources in the geographic area. For example, icons having thunderbolts on them represent AED's that a responder may grab and take to the person when the person has suffered a sudden cardiac arrest. Icons having a "+" on them may represent first aid kits that responders could use to bandage or otherwise treat victims of an accident. Icons having a bold "H" on them may represent hospitals that have equipment and medications important for disaster relief. Icons having a shopping cart on them may represent supermarkets with a supply of fresh water and food that can be delivered to people.

FIG. 3C shows a screenshot of the display of a mobile device 108a, in particular, a smartphone of the emergency responder 102a during an emergency situation. The application on the mobile device 108a has both the basic user module and the responder module installed. The display of the mobile device shows an example of what the emergency responder 102a may see after he/she has been notified about a disaster situation. An emergency responder location is marked and a route 131a to a shelter 106a is displayed. For instance, the central server may provide to the mobile device 108a information to allow the emergency responder 102a to locate his/her highest priority emergency incident, to show any relevant equipment and facilities in the area on the way to the shelter 106a, and to communicate to other responders. In this example, the information has been provided to the responder 102a in the form of a webpage mash-up document that includes custom text 324 about the shelter 106a and its occupants, selectable controls by which the emergency responder 102a may interact with the system, and a map 326 with a navigational route to guide the emergency responder 102a to the storm shelter.

The bottom of the display of the mobile device 108 is taken up by the map 326 which may be generated from a combination of data sources, e.g., using techniques such as those for creating mash-ups with GOOGLE MAPS™. For example, the central server may provide a latitude and longitude for the emergency responder 102a and a latitude and longitude for the shelter 106a, to a navigation system that is publicly available (via a published application programming interface (API)), and a navigation system may respond by providing data for drawing the map overlaid with a thick navigation route line for an optimal path between the two points for the emergency responder 102a. This path may be superimposed on the map 326 that responder 102a is shown. In addition, actual icons 135 and 147 are superimposed on the map to show the emergency responder 102a where relevant resources are located near their route between their current location and the shelter 106a. In this case, a hospital is represented by the icon 135, and a grocery store is represented by icon 147.

The emergency responder 102a may interact with the map 326, e.g., by scrolling or zooming, such as by using a pinch gesture with her fingers so as to see more detail or to see more of the surrounding area. For example, as shown in the figure, the emergency responder 102a is zoomed in too far to see other emergency responders. As a result, responder 102a may want to zoom out so as to see more of the area and to obtain a better overview of what is occurring around his assigned shelter 106a. The particular zoom level that is initially presented to the emergency responder 102a may be selected automatically by the system so that both the location of the emergency responder 102a and of the shelter 106a are shown on the mobile device 108a.

The central server 100 may receive additional information that may be sent out to all users equipped with the responder module regarding updated information on a particular shelter. For example, the dispatcher may have learned that the shelter 106a has a diabetic occupant or has other issues that the emergency responder 102a should be aware of. That information may be provided in the custom text area 324 so that the emergency responders can immediately see it if they are looking at their devices while they run or otherwise make their way toward the shelter 106a. Earlier text may be scrolled upward as additional text is added to the custom text area 324, and a "Communicate with Dispatchers" button 330 may also be shown so as to allow multiple-way communication among the dispatcher and the emergency responders. The emergency responders can request information from the central server via the button 330. The chat text may be populated directly by typing of various users, or by users speaking and their spoken words being converted into text. All such spoken communications between and among the people involved in the event may also be converted in a similar manner to be stored with a summary report for the event.

The central server 100 may gather the information that is overlaid on the map 326 before sending such information to various client devices, or the central server 100 may send information to the mobile devices 108, which may in turn automatically contact third-party mapping and navigation services (e.g., using their on-board applications and/or JavaScript provided to them by the server system) to generate the displays shown here. Client devices can be a device that receives data from or sends data to the server 100, for example, emergency responder computing device 108, civilian computing device 107, connected shelter 106 etc.

Such information may be provided using known techniques, such as asynchronous JavaScript and XML (AJAX), so the emergency responder 102a may interact with the information in a rich manner without requiring multiple downloads of web pages every time the emergency responder asks for additional information or alters the display (e.g., by panning or zooming the map). Also, the information may be provided from multiple sources (e.g., the dispatch system, a voice communication system, a map server, live cam scene video, and the like), either directly to the mobile device 108 or through one of the other services.

In some examples, the application can include additional modules, such as a hospital module to assist hospitals with preparation for and response to the emergency situation.

Figure 4A:
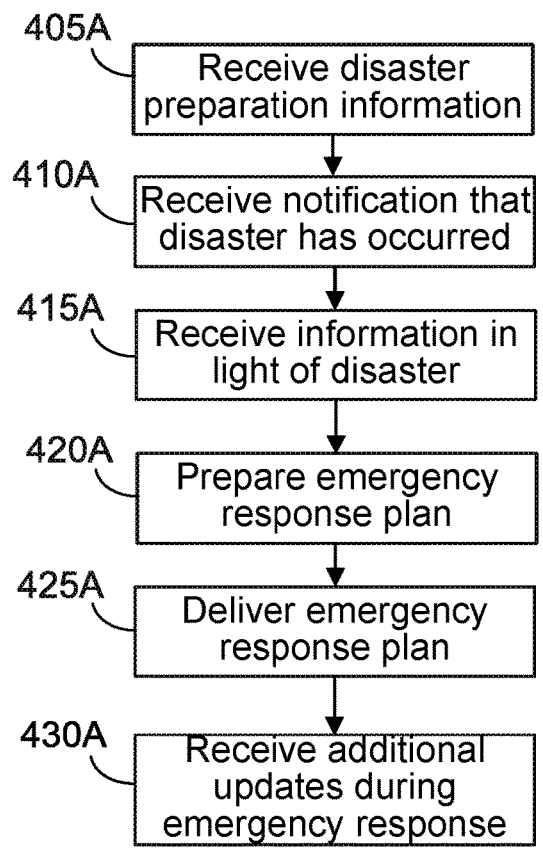
FIGS. 4A and 4B are flow charts.

FIG. 4A is a flow chart of a process executed by one or more computing devices when responding to an emergency situation. In general, the process involves collecting information prior to and during an emergency situation through several sources, processing that information, transmitting relevant information to specific recipients, and continuously providing updates during the emergency response. The process can tracks the actions of emergency responders as they approach the event and attend to a victim or people at the location of the event. The process shown in FIG. 4A can be executed by a single computing device, such as a central server (for example, central server 100), or by a distributed computing system using multiple computing devices. In some examples, one or more features shown in FIG. 4A can be executed by a mobile computing device, such as a mobile computing device operated by an emergency responder.

The server receives information in preparation for an emergency situation (405A). As described earlier, the server can obtain information from a variety of sources, including public databases, emergency responders, civilians, or shelters, or other sources. The server can pre-load information onto mobile devices installed with an emergency response app. For instance, the server can pre-load information about shelter and resource locations onto mobile devices used by emergency responders.

The server receives a notification that an emergency situation has occurred (410A). Examples of disasters can include natural disasters, such as a severe storm, a hurricane, an earthquake; or human-caused disasters, such as a terrorist attack, a nuclear bomb strike, or a chemical spill. The emergency situation can be detected automatically via sensors or be determined by a notification from publically available information or from an individual.

The server receives more information in light of the emergency situation (415A). For instance, the information can include real time information about occupancy of a shelter or confirmation from emergency responders that they are prepared to respond to the emergency incidents. The server can receive current information regarding the emergency situation from news outlets, social media, and other public information outlets. The information may include occupant and shelter status, road closures, environmental and weather conditions, or other information, such as information that may facilitate an efficient emergency response.

The system processes the collected information and prepares an emergency response plan (420A). The emergency response plan may include notifications to users as well as plans for rescue operations. For instance, the system evaluates the information pertaining to each shelter and makes a determination of a priority for emergency response for each shelter based on that information. The evaluation and determination can account for attributes of the people located at each shelter. The system then assigns a highest priority shelter to each emergency responder. The system can consider one or more factors in assigning highest priority shelters, including the shelter status, the status of occupants of the shelter, emergency responder location and expertise, or environmental factors. The possible responders to emergency incidents may be determined based solely on distance from the locations of the emergency incidents, such as by circumscribing a circle of a particular radius around the event (where the circle can be made larger and larger until a predetermined number of potential responders can be found). The emergency responders may be selected based on their estimated time to respond, so that a system could look at the current speed of an emergency responder to infer that the emergency responder is in an automobile, and thus could arrive at the emergency incident more quickly than an emergency responder who is not currently moving.

The server delivers the emergency response plan to emergency responders (425A). The system can selectively distribute information. The information may include some basic information about the emergency situation, updated information from shelters or shelter occupants, information about other emergency responders, or information needed to generate an annotated map (e.g., the map shown in FIG. 1B). Information delivered to responders may include routing details to their highest priority shelters. The system can send map data for transmission to the emergency responders.

The system receives additional updates and continues to disseminate processed updates (430A). The system may receive notification from a shelter occupant or an emergency responder causing a shift in priority for a shelter. For example, the occupants of a shelter may no longer require assistance, or a shelter occupant may indicate that a shelter has become dangerous for residence. The system may also receive notification of additional shelters that have been discovered or reported during the disaster. Such notifications may come from public access information or directly from occupants who are reporting their shelter during the disaster. The system may also receive updates from emergency responders. An example notification may be that an emergency responder may indicate that a rescue operation has been successfully executed or that an emergency responder is experiencing an unforeseen delay. After receiving updates, the system continuously processes the new information and adjusts the emergency response plan as appropriate.

Figure 4B:
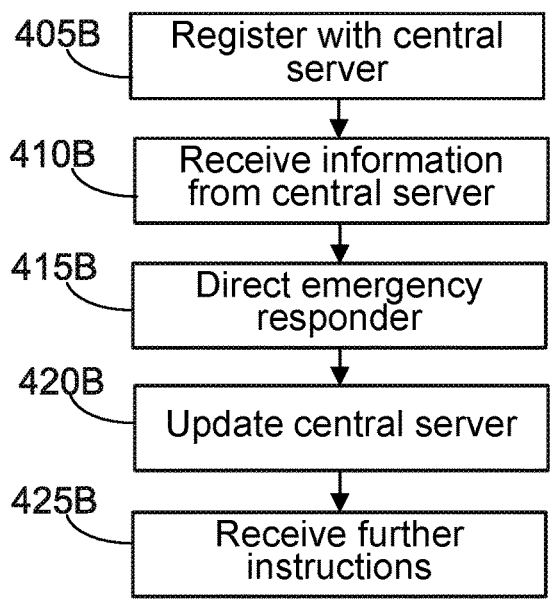

FIG. 4B is an example flow chart of a process for an emergency responder equipped with a mobile device to respond to a disaster. The process shown in FIG. 4B can be executed by a single computing device, such as a mobile computing device operated by an emergency responder, or by a distributed computing system using multiple computing devices.

The emergency responder registers with the central server (405B). Registration may entail downloading an application to her mobile device that permits a central server to communicate with the mobile device. The emergency responder can create a profile indicating characteristics such as her expertise and availability. In some examples, the mobile device is continuously transmitting location information to the central server and receiving push updates from the central server. In some examples, the mobile device can receive text notifications from the central server and send text updates to the central server. The central server can pre-load the mobile device with information in the event that an emergency situation occurs and communication networks have been compromised.

During or after an emergency situation, the mobile device receives updated information from the central server and continues transmitting information to the central server (410B). For example, the emergency responder may have been injured during the disaster and has communicated the injury to the central server, indicating she is not available to execute a rescue operation. The updated information can include information indicative of shelters or shelter occupants.

The mobile device provides instructions to the emergency responder (415B), e.g., according to instructions received from the central server. For instance, the mobile device can direct the emergency responder to her highest priority shelter and recommend the emergency responder to stop by a hospital on route to the shelter in order to retrieve important medication and first aid materials.

The emergency responder continues to update the central server with information pertaining to the rescue operation at her highest priority shelter (420B). For example, she may notify the central server that she has arrived at the shelter and rescued the occupants. The emergency responder may indicate to the central server via her mobile device that a rescue operation has been executed successfully and the occupants of the shelter are in stable condition. However, the emergency responder might also indicate that she is experiencing delays and may need to be assigned a different shelter due to the delays.

The emergency responder receives further instructions from the central server (425B), indicating to the emergency responder, e.g., to attend to another high priority shelter or to assist another emergency responder with a rescue operation.

Figure 5:
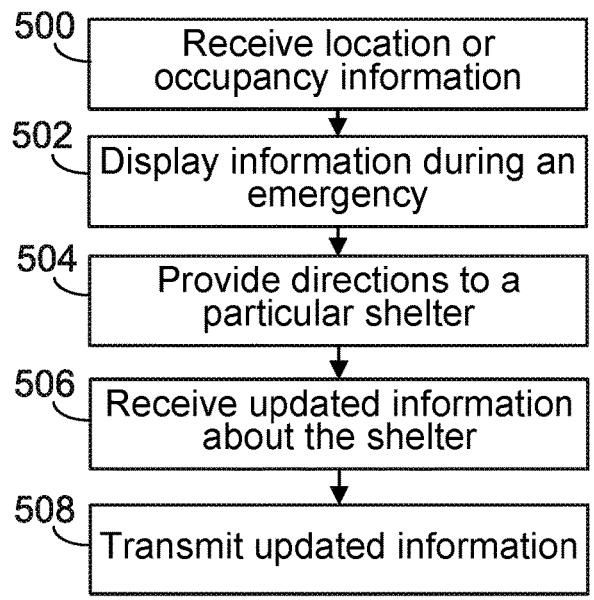
FIG. 5 is a flow chart.

Referring to FIG. 5, in an example process, information indicative of one or more of the location of one or more shelters or the potential occupancy of one or more of the shelters prior to an emergency situation is received (500). During an emergency, information is displayed on an interface of a computing device, such as a defibrillator or mobile computing device (502). The information can include the information indicative of one or more of the location of one or more shelters or the potential occupancy of one or more of the shelters prior to an emergency situation. Based on a location of the computing device and the information indicative of the location of a particular shelter, directions to the particular shelter are provided (504). Updated information indicative of the actual occupancy of the particular shelter is received (506). The updated information is transmitted to a remote computing device (508). The process shown in FIG. 5 can be executed by a single computing device, such as a mobile computing device operated by an emergency responder, or by a distributed computing system using multiple computing devices.

While the emergency responder devices 108 are shown and described as a mobile devices in this example, it may take a variety of other forms. For example, the device could be a cellular telephone having text messaging capabilities, so that the user can receive direction via text message. The device could also be a portable networked device that does not have direct telephony capabilities such as an IPOD TOUCH media player or similar device. Other devices such as tablet PC's and other portable communication devices may also be used. In addition, certain of the functionality described above and below can be provided as part of an accessory to the relevant electronic communication, such as by placing a force sensor, temperature sensor, accelerometer, pulse sensor, blood pressure sensor, or other sensor in a plug-in module and/or jacket that a user can purchase for their electronic communication device (though such sensors may also be integrated into the device where appropriate). For example, a user of device may purchase an electronic stethoscope that may plug into device and act as a traditional stethoscope. A user may also purchase a blood-pressure cuff or other such sensors that may provide electronic signals to device so that readings of victim parameters, and particularly vital signs, may be uploaded easily to the rest of the system through the network.

In addition, other normal components of a smart phone or other communication device could be used as relevant sensors. For example, a pressure sensitive touch screen could be used as a force sensor by accessing, through the device's operating system, signals coming from the screen. Where the screen is a capacitive or impedance-based touch screen, the sensed signals could also be used for pulse measurements. For example, the field lines from such a screen extend outward from the front of the screen, and the screen could be pressed against the side of a victim's (or other person's) neck to measure changes caused by the periodic rush of blood through the victim's carotid artery. Touch screen sensors are also two-dimensional sensors, so that the exact positioning of the device would not be critical, and irregularities in positioning could be adjusted for by the software on the device. Such measurements could then be reported back to a central system automatically, such as to communicate the victim's vital signs to professional responders or to remote medical professionals who can advise the lay responders, including physicians at a hospital where the victim is likely to be transported.

The systems and techniques described here can also be employed in a situation in which there are mass casualties, such as a large accident (e.g., train, bus, or airplane crash), a terrorist attack (e.g., bombing or gas dispersion), natural disaster (e.g., earthquake or large tornado), or public health crisis. For example, the system may initially determine manually, automatically, or semi-automatically, that an emergency situation in the form of a mass event is occurring, such as by determining that a number of calls for different events (e.g., different people in need of held) over a time period (e.g., 1 hour) and in a particular area has exceeded a predetermine threshold. Such a determination may be made by using known automatic clustering analysis techniques so as to distinguish calls that are connected as shown by time and geographic location, from those that are independent but happen to be spatially and time related. Upon the condition of a mass event being recognized, the system may generate an alarm via the communications systems to begin elevating the status of the event. For example, the alarm may first be provided to a dispatcher or dispatchers who may attempt to confirm the nature of the event, such as by asking a victim at the scene a series of questions designed to elicit information about the type of event and scope of the event. At a next stage, the emergency responder system described herein is executed.

The features described herein can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented on a mobile computing device, such as a mobile phone, a tablet, a wearable computing device (e.g., a wrist-worn computing device such as a watch, glasses, a visor, a face mask, an ear piece, an article of clothing, or another type of wearable computing device), or another type of mobile computing device. The mobile computing device can have a display device such as a touch screen for displaying information to the user and receiving input from the user. The mobile computing device can receive input from the user via the touch screen, a key pad, a microphone, or another type of input device.

A wearable computing device can provide the functionality of receiving, transmitting, and/or displaying data. Data processing may also be provided by such a wearable computing device (e.g., processing received data prior to display, processing data prior to sending to another computing device, etc.). In some instances, a wearable computing device can take the form of a head-mounted device that can include frame elements including lens-frames, a center support, one or more lenses, and side supports (for securing the device to a user). The wearable computing device may additionally include an on-board computing system, a still or video camera (mountable to the device at various locations), speakers, etc. The on-board computing system may have the capability to communicate with other computing devices, systems, etc. external to the wearable computing device, e.g., through a wireless network connection, a short-range (e.g., Bluetooth) connection, a cellular connection, or another type of connection.

Various techniques may be employed to exchange information between the wearable computing device and the wearer. For example, the wearable computing device may include one or more displays that may be coupled to the device. Such a display may be formed on one lens or multiple lenses of the wearable computing device and may be configured to overlay computer-generated images, graphics, etc. in the user's view of the physical world. The display can be positioned at one or more locations of the lens or lenses, for example, at the center of one or more of the lens. In general, the display is controllable by the on-board computing system and is in communication with the computing system by employing one or more data transmission techniques (e.g., an optical waveguide or fiber, electrical conductor, etc.). In some arrangements, the frame of the wearable computing device can be similar to a frame of a pair of glasses (e.g., prescription glasses, sunglasses, reading glasses, etc.). In some instances, the lenses incorporated into the device may be less than a completely formed lenses typically included in eyeglasses. Due to the less than complete lens or lenses, the device may not include a lower frame portion typically used to secure a complete lens to the frame.

To interact with the wearable computing device, one or more techniques may be employed. For example, a touch-based input (e.g., a touchpad) may be incorporated to sense the position and movement of a user's finger by capacitive sensing, resistance sensing, or other techniques. Equipment (e.g., one or more acceleration sensors) may be incorporated to sense the movement of a portion of the user (e.g., the user's head). One or more microphones may also be incorporated into the device to collect audible signals (e.g., voice commands) from the user. Similar to sensing position and movement, the direction of a user's finger (interacting with the touch-based input), the level of applied pressure, etc. may be sensed by interacting with device input.

In some arrangements, the wearable computing device can provide networking functionality. For example, the wearable device can be used to provide a node of a network architecture (e.g., a node for a mesh network). As such, information can be exchanged with (e.g., transmitted to, received from) other network nodes (e.g., other wearable computing devices at nearby locations, mobile computing devices, medical devices such as defibrillating systems, wearable medical devices, etc.). In one arrangement, multiple members of an emergency response team may each be outfitted with a wearable computing device that provides a network node. By employing data transmission techniques (e.g., one or more network protocols), information may be shared among the wearable computing devices, e.g., so each member is provided the same information during the emergency or so that information can be exchanged among members during the emergency.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The network can take the form of an ad hoc, self-configuring, self-healing network such as a MESH network. Wireless mesh networks are multihop systems in which devices assist each other in transmitting packets through the network, especially in adverse conditions. Such ad hoc networks may be implemented with minimal preparation, and they can provide a reliable, flexible system that can be extended to thousands of devices.

In a wireless mesh network, multiple nodes cooperate to relay a message to its destination. The mesh topology enhances the overall reliability of the network, which is particularly important when operating in harsh industrial environments. Like the Internet and other peer-to-peer router-based networks, a mesh network offers multiple redundant communications paths throughout the network. If one link fails for any reason (including the introduction of strong RF interference), the network automatically routes messages through alternate paths. In a mesh network, the distance between nodes can be shortened, which dramatically increases the link quality. Reducing the distance by a factor of two, the resulting signal is at least four times more powerful at the receiver. This makes links more reliable without increasing transmitter power in individual nodes. The reach of a mesh network may be extended, redundancy added, and general reliability improved simply by adding more notes.

A network may be a self-configuring and self-healing network. A network may not require a system administrator to tell it how to get a message to its destination. A mesh network can be self-organizing and does not require manual configuration. Because of this, adding new gear or relocating existing gear is as simple as plugging it in and turning it on. The network can discover the new node and automatically incorporates it into the existing system.

A mesh network is not only inherently reliable, it can also be highly adaptable. For example, if a tank-level sensor and data logger are placed too far apart for a robust RF communications link, one or more repeater nodes may be added to fill the gaps in the network.

On the Internet, if one router goes down, messages are sent through an alternate path by other routers. Similarly, if a device or its link in a mesh network fails, messages are sent around it via other devices. Loss of one or more nodes does not necessarily affect the network's operation. A mesh network is self-healing because human intervention is not necessary for re-routing of messages. Such networks provide redundancy and scalability.

In a mesh network, the degree of redundancy is essentially a function of node density. A network can be deliberately over-designed for reliability simply by adding extra nodes, so each device has two or more paths for sending data. This is a simpler way of obtaining redundancy than is possible in most other types of systems. A mesh network is also scalable and can handle hundreds or thousands of nodes. Because the operation of network does not depend on a central control point, adding multiple data collection points or gateways may be convenient.

Reliability, adaptability, and scalability are notable attributes of a wireless network for industrial control and sensing applications. Point-to-point networks provide reliability, but they are often challenging to scale to handle more than one pair of end points. Point-to-multipoint networks can handle more end points, but their reliability may depend on placement of the access point and end points. Mesh networks are inherently reliable, adapt easily to environmental or architectural constraints, and can scale to handle thousands of end points.

The computer system can include clients and servers. A client and server are generally remote from each other and typically interact through a network, such as the described one. The relationship of client and server arises by virtue of computer programs running on the respective computers and having a client-server relationship to each other.

Other features are in the scope of the following claims.

What is claimed is:

1. A system comprising:
    a shelter registry configured to store data about a plurality of shelters;
    one or more emergency responder computing devices; and
    a server in communication with the shelter registry, the one or more emergency responder computing devices, and one or more civilian computing devices, the server configured to:
        store information related to civilians who have registered with one or more of the plurality of shelters or who live or work within a threshold distance of the one or more of the plurality of shelters;
        determine, based on the stored information related to the civilians, a potential occupancy of the one or more of the plurality of shelters, wherein the potential occupancy represents a number of potential occupants expected to take shelter at the respective shelter during an emergency situation and medical condition information of at least one potential occupant;
        receive, from the one or more civilian computing devices, historical location information comprising a plurality of periodically transmitted location data during a past time interval followed by a recent time interval characterized by absence of transmission of current location information;
        determine predicted current location information during the recent time interval based on the historical location information;
        receive, from the shelter registry, location information indicative of locations of the one or more of the plurality of shelters and medical device information comprising distribution of medical devices within the one or more of the plurality of shelters;
        determine occupancy information related to an actual occupancy of the one or more of the plurality of shelters and medical information of occupants, wherein the actual occupancy is based at least in part on the predicted current location information and the medical information of occupants comprises at least one of: medical history, medical conditions, and ongoing medical events;
        determine a medical need of the plurality of shelters based on the medical condition information of the at least one potential occupant;
        prioritize the one or more of the plurality of shelters as needing attention based at least in part on the medical information of occupants, the medical device information, the potential occupancy, the actual occupancy of the one or more of the plurality of shelters, and the determined medical need of the one or more of the plurality of shelters;
        receive, from the one or more emergency responder computing devices, responder information comprising available medical devices;
        generate an assignment of one or more emergency responders to the prioritized shelters based on the responder information, the determined medical need of the one or more of the plurality of shelters, and emergency responder expertise, comprising:
            determining an estimated time of arrival of the one or more emergency responders to the prioritized shelters based on a location and speed of corresponding ones of the one or more emergency responder computing devices;
            determining whether the one or more emergency responders have the expertise for treating the determined medical need; and
            assigning the one or more emergency responders to the prioritized shelters based on their estimated time to respond; and
        provide, to the one or more emergency responder computing devices, the information indicative of the location of one of the prioritized shelters based on assignment of one or more emergency responders to the prioritized shelters and filtered medical information based on the medical information of occupants and the medical device information, wherein each of the one or more emergency responder computing devices is configured to present, on a display of the emergency responder computing device, the filtered medical information and a graphical map representation of the location of the one of the prioritized shelters, a location of the emergency responder computing device, and directions for navigating from the location of the emergency responder computing device to the one of the prioritized shelters.

2. The system of claim 1, in which the one or more emergency responder computing devices are configured to periodically receive historical location data to predict the potential occupancy for the plurality of shelters.

3. The system of claim 2, in which the historical location data of the people identified for the potential occupancy is stored prior to the emergency situation.

4. The system of claim 1, in which the one or more emergency responder computing devices and the one or more civilian computing devices are mobile computing devices.

5. The system of claim 4, in which the mobile computing device comprises a wearable computing device.

6. The system of claim 1, in which a user interface of the one or more emergency responder computing devices comprises a medical user interface of a medical device.

7. The system of claim 6, in which the medical device comprises a defibrillator.

8. The system of claim 1, in which the potential occupancy comprises one or more of an identity of at least one of the potential occupants of the respective shelter, and demographic information about the potential occupants of the respective shelter.

9. The system of claim 1, in which the information related to the actual occupancy of the plurality of shelters comprises one or more of a number of actual occupants of the plurality of shelters, an identity of at least one of the actual occupants of the plurality of shelters, demographic information about the potential occupants of the plurality of shelters, a medical condition of at least one of the actual occupants of the plurality of shelters, and a health status of at least one of the actual occupants of the plurality of shelters.

10. The system of claim 1, in which the information indicative of the location of the one or more of the plurality of shelters includes one or more of GPS coordinates, an address, a landmark, and a property description.

11. The system of claim 1, in which the one or more emergency responder computing devices are configured to:
receive an input identifying a particular shelter of the plurality of shelters; and
cause display of information indicative of the location of the particular shelter.

12. The system of claim 11, in which the one or more emergency responder computing devices are configured to receive the input from the one or more emergency responders through the user interface.

13. The system of claim 11, in which the one or more emergency responder computing devices are configured to receive the input from a remote computing device.

14. The system of claim 1, in which the one or more emergency responder computing devices are configured to identify a particular shelter of the plurality of shelters to which the one or more emergency responders can provide rescue services.

15. The system of claim 14, in which the one or more emergency responder computing devices are configured to identify the particular shelter based on a location of the one or more emergency responders and a location of the particular shelter.

16. The system of claim 14, in which the particular shelter is the one of the prioritized shelters, and the one or more emergency responder computing devices are configured to identify the particular shelter based on the actual occupancy of the one of the prioritized shelters.

17. The system of claim 14, in which the one or more emergency responder computing devices are configured to identify the particular shelter based on one or more of an expertise of the one or more emergency responders and a piece of medical equipment available to the one or more emergency responders.

18. The system of claim 14, in which the particular shelter is identified based on the prioritized shelters, the priority being determined using a multivariate optimization technique and is based on an expertise of the one or more emergency responders and environmental conditions near the one or more of the plurality of shelters.

19. The system of claim 1, in which the directions are determined based on information indicative of road status.

20. The system of claim 19, in which the one or more emergency responder computing devices are configured to receive the information indicative of road status during the emergency situation.

21. The system of claim 1, in which the one or more emergency responder computing devices are configured to receive one or more of (i) updated information indicative of the location of the one of the prioritized shelters, and (ii) updated information indicative of the actual occupancy of the one of the prioritized shelters.

22. The system of claim 21, in which the one or more emergency responder computing devices are configured to transmit the updated information to a remote computing device.

23. The system of claim 1, in which historical location data is periodically received to predict the potential occupancy.

24. The system of claim 1, wherein the potential occupancy represents a number of people expected to be near the respective shelter, and the potential occupancy is determined at least in part based on user inputs indicating intentions of fleeing to the respective shelter.

25. The system of claim 1, wherein the server is in communication with at least the shelter registry over a mesh network configured to adapt to environmental or architectural constraints to dynamically modify a number of communication points included in the mesh network for data transmission.

26. The system of claim 1, wherein each of the one or more emergency responder computing devices is configured to subsequently present updated information on the display based on an updated priority of the plurality of shelters.

27. The system of claim 26, wherein the one of the prioritized shelters is determined as being a highest priority shelter at the server based at least in part on information received from the one or more emergency responder computing devices related to a status of a rescue operation.

28. The system of claim 1, wherein civilians are identified as having registered with the one or more of the plurality of shelters based on input received through an emergency response application executing on the one or more civilian computing devices.

29. The system of claim 1, wherein a particular shelter of the prioritized shelters is identified as needing attention for each of the one or more emergency responder computing devices.

30. The system of claim 29, wherein the particular shelter is identified based on the location of the particular shelter and the location of the respective emergency responder computing device.

31. The system of claim 1, wherein the server is configured to provide, to the one or more emergency responder computing devices, information indicative of the actual and potential occupancy of the one of the prioritized shelters.

32. The system of claim 1, wherein the server is configured to provide, to the one or more emergency responder computing devices, information related to one or more relevant resources in an area on a way to the one of the prioritized shelters.

33. The system of claim 32, wherein the graphical map representation includes a representation of a location of the one or more relevant resources.

34. The system of claim 32, wherein the one or more relevant resources include food, water, a first aid kit, and a defibrillator.

35. The system of claim 1, wherein the server is configured to provide, to the one or more emergency responder computing devices, information related to one or more relevant facilities in an area on a way to the one of the prioritized shelters.

36. The system of claim 35, wherein the graphical map representation includes a representation of a location of the one or more relevant facilities.

37. The system of claim 35, wherein the one or more relevant facilities includes one or both of a healthcare facility or a shopping facility.

38. The system of claim 1, wherein the actual occupancy is based at least in part on locations of the one or more civilian computing devices relative to the respective shelter determined by occupancy sensors that are in communication with the server.

39. The system of claim 1, wherein the map is displayed by each of the one or more emergency responder computing devices at a zoom level selected automatically by the server based on a distance between the respective emergency responder computing device and the prioritized shelters.

40. The system of claim 1, wherein the server is configured to:
determine whether the medical devices within the prioritized shelters are available to provide medical treatment to satisfy the medical need of the prioritized shelter based on the medical device information stored in the shelter registry; and
responsive to determining that medical devices within the plurality of shelters are unavailable, providing navigational instructions to the one or more emergency responder computing devices for presenting a navigational path to a location with available medical devices, wherein the available medical devices are usable to further satisfy the medical need of the prioritized shelter.

41. A non-transitory computer readable storage medium storing instructions for causing a computing system to:
store information related to civilians who have registered with one or more of a plurality of shelters or who live or work within a threshold distance of the one or more of the plurality of shelters;
determine, based on the stored information related to the civilians, a potential occupancy of the one or more of the plurality of shelters, wherein the potential occupancy represents a number of potential occupants expected to take shelter at the respective shelter during an emergency situation and medical condition information of at least one potential occupant;
receive, from the one or more civilian computing devices, historical location information comprising a plurality of periodically transmitted location data during a past time interval followed by a recent time interval characterized by absence of transmission of current location information;
determine predicted current location information during the recent time interval based on the historical location information;
receive, from the shelter registry, location information indicative of locations of the one or more of the plurality of shelters and medical device information comprising distribution of medical devices within the one or more of the plurality of shelters;
determine occupancy information related to an actual occupancy of the one or more of the plurality of shelters and medical information of occupants, wherein the actual occupancy is based at least in part on the predicted current location information and the medical information of occupants comprises at least one of: medical history, medical conditions, and ongoing medical events;
determine a medical need of the plurality of shelters based on the medical condition information of the at least one potential occupant;
prioritize the one or more of the plurality of shelters as needing attention based at least in part on the medical information of occupants, the medical device information, the potential occupancy, the actual occupancy of the one or more of the plurality of shelters, and the determined medical need of the one or more of the plurality of shelters;
receive, from the one or more emergency responder computing devices, responder information comprising available medical devices;
generate an assignment of one or more emergency responders to the prioritized shelters based on the responder information, the determined medical need of the one or more of the plurality of shelters, and emergency responder expertise, comprising:
determining an estimated time of arrival of the one or more emergency responders to the prioritized shelters based on a location and speed of corresponding ones of the one or more emergency responder computing devices;
determining whether the one or more emergency responders have the expertise for treating the determined medical need; and
assigning the one or more emergency responders to the prioritized shelters based on their estimated time to respond; and
provide, to one or more emergency responder computing devices, the information indicative of the location of one of the prioritized shelters based on assignment of one or more emergency responders to the prioritized shelters and filtered medical information based on the medical information of occupants and the medical device information,
wherein each of the one or more emergency responder computing devices is configured to present, on a display of the emergency responder computing device, the filtered medical information and a graphical map representation of the location of the one of the prioritized shelters, a location of the emergency responder computing device, and directions for navigating from the location of the emergency responder computing device to the one of the prioritized shelters.

42. The non-transitory computer readable storage medium of claim 41, in which the instructions cause the computing system to periodically receive historical location data to predict the potential occupancy for the plurality of shelters.

43. The non-transitory computer readable storage medium of claim 42, in which the instructions cause the computing system to receive and store the historical location data of people identified for the potential occupancy prior to the emergency situation.

44. The non-transitory computer readable storage medium of claim 42, in which the one or more emergency responder computing devices and the one or more civilian computing devices are mobile computing devices.

45. The non-transitory computer readable storage medium of claim 44, in which the mobile computing device comprises a wearable computing device.

46. The non-transitory computer readable storage medium of claim 41, in which a user interface of the one or more emergency responder computing devices comprises a medical user interface of a medical device.

47. The non-transitory computer readable storage medium of claim 46, in which the medical device comprises a defibrillator.

48. The non-transitory computer readable storage medium of claim 41, in which the potential occupancy comprises one or more of an identity of at least one of the potential occupants of the shelter, and demographic information about the potential occupants of the shelter.

49. The non-transitory computer readable storage medium of claim 41, in which the information related to the actual occupancy of the one or more of the plurality of shelters comprises one or more of a number of actual occupants of the shelter, an identity of at least one of the actual occupants of the shelter, demographic information about the potential occupants of the shelter, a medical condition of at least one of the actual occupants of the shelter, and a health status of at least one of the actual occupants of the shelter.

50. The non-transitory computer readable storage medium of claim 41, in which the information indicative of the location of the one or more of the plurality of shelters includes one or more of GPS coordinates, an address, a landmark, and a property description.

51. The non-transitory computer readable storage medium of claim 41, in which the instructions cause the computing system to:
receive an input identifying a particular shelter of the plurality of shelters; and
cause display of information indicative of the location of the particular shelter.

52. The non-transitory computer readable storage medium of claim 51, in which the instructions cause the computing system to receive the input from the one or more emergency responders through a user interface.

53. The non-transitory computer readable storage medium of claim 51, in which the instructions cause the computing system to receive the input from a remote computing device.

54. The non-transitory computer readable storage medium of claim 41, in which the instructions cause the computing system to identify a particular shelter of the plurality of shelters to which the one or more emergency responders can provide rescue services.

55. The non-transitory computer readable storage medium of claim 54, in which the instructions cause the computing system to identify the particular shelter based on a location of the one or more emergency responders and a location of the particular shelter.

56. The non-transitory computer readable storage medium of claim 54, in which the particular shelters is the one of the prioritized shelters, and the instructions cause the computing system to identify the particular shelter based on the actual occupancy of the one of the prioritized shelters.

57. The non-transitory computer readable storage medium of claim 54, in which the instructions cause the computing system to identify the particular shelter based on one or more of an expertise of the one or more emergency responders and a piece of medical equipment available to the one or more emergency responders.

58. The non-transitory computer readable storage medium of claim 41, in which the instructions cause the computing system to determine the directions based on information indicative of road status.

59. The non-transitory computer readable storage medium of claim 58, in which the instructions cause the computing system to receive the information indicative of road status during the emergency situation.

60. The non-transitory computer readable storage medium of claim 41, in which the instructions cause the computing system to receive one or more of (i) updated information indicative of the location of the one of the prioritized shelters, and (ii) updated information indicative of the actual occupancy of the one of the prioritized shelters.

61. The non-transitory computer readable storage medium of claim 60, in which the instructions cause the computing system to transmit the updated information to a remote computing device.

62. A method comprising:
storing information related to civilians who have registered with one or more of a plurality of shelters or who live or work within a threshold distance of the one or more of the plurality of shelters;
determining, based on the stored information related to the civilians, a potential occupancy of the one or more of the plurality of shelters, wherein the potential occupancy represents a number of potential occupants expected to take shelter at the respective shelter during an emergency situation and medical condition information of at least one potential occupant;
receiving, from the one or more civilian computing devices, historical location information comprising a plurality of periodically transmitted location data during a past time interval followed by a recent time interval characterized by absence of transmission of current location information;
determining predicted current location information during the recent time interval based on the historical location information;
receiving, from the shelter registry, location information indicative of locations of the one or more of the plurality of shelters and medical device information comprising distribution of medical devices within the one or more of the plurality of shelters;
determining occupancy information related to an actual occupancy of the one or more of the plurality of shelters and medical information of occupants, wherein the actual occupancy is based at least in part on the predicted current location information and the medical information of occupants comprises at least one of: medical history, medical conditions, and ongoing medical events;

determining a medical need of the plurality of shelters based on the medical condition information of the at least one potential occupant;

prioritizing the one or more of the plurality of shelters as needing attention based at least in part on the medical information of occupants, the medical device information, the potential occupancy, the actual occupancy of the one or more of the plurality of shelters and the determined medical need of the one or more of the plurality of shelters;

receiving, from the one or more emergency responder computing devices, responder information comprising available medical devices;

generating an assignment of one or more emergency responders to the prioritized shelters based on the responder information, the determined medical need of the one or more of the plurality of shelters, and emergency responder expertise, comprising:

determining an estimated time of arrival of the one or more emergency responders to the prioritized shelters based on a location and speed of corresponding ones of the one or more emergency responder computing devices;

determining whether the one or more emergency responder have the expertise for treating the determined medical need; and assigning the one or more emergency responders to the prioritized shelters based on their estimated time to respond; and providing, to the one or more emergency responder computing devices, the information indicative of the location of one of the prioritized shelters based on assignment of one or more emergency responders to the prioritized shelters and filtered medical information based on the medical information of occupants and the medical device information, wherein each of the one or more emergency responder computing devices is configured to present, on a display of the emergency responder computing device, the filtered medical information and a graphical map representation of the location of the one of the prioritized shelters, a location of the emergency responder computing device, and directions for navigating from the location of the emergency responder computing device to the one of the prioritized shelters.

* * * * *